United States Patent [19]
Goodrich, Jr. et al.

[11] Patent Number: 5,958,670
[45] Date of Patent: Sep. 28, 1999

[54] METHOD OF FREEZING CELLS AND CELL-LIKE MATERIALS

[75] Inventors: Raymond P. Goodrich, Jr., Pasadena; Samuel O.S. Coker, South Pasadena; Francoise Arnaud; Roger W. Hackett, both of Pasadena, all of Calif.

[73] Assignee: COBE Laboratories, Inc., Lakewood, Colo.

[21] Appl. No.: 08/260,165

[22] Filed: Jun. 15, 1994

Related U.S. Application Data

[63] Continuation of application No. 07/824,116, Jan. 21, 1992, abandoned, which is a continuation-in-part of application No. 07/705,622, May 25, 1990, abandoned, and a continuation-in-part of application No. 07/528,955, May 25, 1990, abandoned, and a continuation-in-part of application No. 07/505,255, Apr. 5, 1990, Pat. No. 5,153,004, which is a continuation-in-part of application No. 07/361,023, Jun. 2, 1989, abandoned, and a continuation-in-part of application No. 07/525,392, May 17, 1990, Pat. No. 5,213,814, which is a continuation-in-part of application No. 07/378,349, Jul. 11, 1989, Pat. No. 5,045,446, which is a continuation-in-part of application No. 07/237,583, Aug. 25, 1988, abandoned, and a continuation-in-part of application No. 07/360,386, Jun. 2, 1989, Pat. No. 5,043,261, which is a continuation of application No. 07/335,557, Apr. 10, 1989, abandoned, which is a continuation-in-part of application No. 07/195,745, May 18, 1988, abandoned, and a continuation-in-part of application No. 07/237,583, Aug. 25, 1988, abandoned, and a continuation-in-part of application No. 07/374,171, Jun. 29, 1989, Pat. No. 5,178,884, which is a continuation-in-part of application No. 07/360,386, Jun. 2, 1989, Pat. No. 5,043,261.

[51] Int. Cl.$^6$ ............... A01N 1/02; C12N 5/00; G01N 31/00

[52] U.S. Cl. ............... 435/2; 435/1.3; 435/325; 466/18

[58] Field of Search ............... 435/1, 2, 240.1, 435/325, 1.3; 436/18

[56] References Cited

U.S. PATENT DOCUMENTS

| | | | |
|---|---|---|---|
| 4,865,871 | 9/1989 | Livesey et al. | 435/1 |
| 5,004,681 | 4/1991 | Boyse et al. | |
| 5,045,446 | 9/1991 | Goodrich et al. | 435/2 |
| 5,084,377 | 1/1992 | Rowan et al. | 435/1 |
| 5,098,893 | 3/1992 | Franks et al. | 514/54 |
| 5,145,770 | 9/1992 | Tubo et al. | |
| 5,153,004 | 10/1992 | Goodrich, Jr. et al. | |
| 5,178,884 | 1/1993 | Goodrich et al. | |
| 5,192,553 | 3/1993 | Boyse et al. | |
| 5,242,792 | 9/1993 | Rudolph et al. | 435/1 |

FOREIGN PATENT DOCUMENTS

| | | |
|---|---|---|
| 475409 A2 | 3/1992 | European Pat. Off. |
| 1057277 | 2/1967 | United Kingdom |
| 1279356 | 6/1972 | United Kingdom |
| 2046772 | 11/1980 | United Kingdom |
| WO 87/05300 | 9/1987 | WIPO |
| B-42837 | 10/1989 | WIPO |
| B-44118 | 10/1989 | WIPO |
| WO 90/09432 | 8/1990 | WIPO |
| WO91/18505 | 12/1991 | WIPO |

OTHER PUBLICATIONS

H. Levine et al., Water Science Reviews, 3:79–185, Cambridge Univ. Press Cambridge 1988.
H. Levine et al., Cryo–Letters, 9:21–63 (1988).
F. Franks, Stability of Proteins Theory and Practice, Jul. 1–5, 1991, Cambridge, U.K.
F. Franks, Develop. Biol. Standard, 74:9–19 (Karger, Basel 1991).
M. Pikal, BioPharm, pp. 18–27 (Sep. 1990).
KryoHAES® Zur Kryokonservierung von Human–Erythrozyten mit Hydroxyethylstärke (HES), Fresenius.
Freeze–Drying of Red Blood Cells, Advances in Low–Temperature Biology, vol. 2, pp. 53–99, Raymond P. Goodrich and Samuel O. Sowemimo–Coker.
U.A. Brodthagen et al., "Platelet Cryopreservation with Glycerol, Dextran, and Mannitol: Recovery of 5–Hydroxytryptamine Uptake and Hypotonic Stress Response", *Cryobiology*, vol. 22, pp. 1–9, (1985).
J.A. Smillie et al., "Cryopreservation of Human Platelets with Polyvinylpyrrolidone", *Transfusion*, vol. 21, No. 5, pp. 552–556, (1981).
Mar. 5, 1993 International Search Report.
Jan. 3, 1995 International Search Report.

*Primary Examiner*—Leon B. Lankford, Jr.
*Attorney, Agent, or Firm*—Finnegan, Henderson, Farabow, Garrett & Dunner, L.L.P.

[57] ABSTRACT

A process is provided for freezing, including freeze-drying of cells, cell-membranes or cell-like materials using a cryoprotectant medium which stabilizes the cells or membranes for freezing or freeze-drying and allows for freezing or freeze-drying to be performed at −60° C. or higher.

49 Claims, 5 Drawing Sheets

METHOD OF FREEZING CELLS AND CELL-LIKE MATERIALS

This is a continuation of application Ser. No. 07/824,116 filed Jan. 21, 1992, abandoned which is a continuation-in-part of Ser. No. 07/705,622, filed May 25, 1990, now abandoned and a continuation-in-part of Ser. No. 07/528,955, filed May 25, 1990, now abandoned and a continuation-in-part of Ser. No. 07/505,255, filed Apr. 5, 1990, now U.S. Pat. No. 5,153,004 which is a continuation-in-part of Ser. No. 07/361,023, filed Jun. 2, 1989, now abandoned and a continuation-in-part of Ser. No. 07/525,392, filed May 17, 1990, now U.S. Pat. No. 5,213,814 which is a continuation-in-part of Ser. No. 07/378,349, filed Jul. 11, 1989, now U.S. Pat. No. 5,045,446 which is a continuation-in-part of Ser. No. 07/237,583, filed Aug. 25, 1988, now abandoned and a continuation-in-part of Ser. No. 07/360,386, filed Jun. 2, 1989, now U.S. Pat. No. 5,043,261 which is a continuation of Ser. No. 07/335,557, filed Apr. 10, 1989, now abandoned which is a continuation-in-part of Ser. No. 07/195,745, filed May 18, 1988, now abandoned and a continuation-in-part of Ser. No. 07/237,583, filed Aug. 25, 1988, now abandoned and a continuation-in-part of Ser. No. 07/374,171 filed Jun. 29, 1989, now U.S. Pat. No. 5,178,884 which is a continuation-in-part of Ser. No. 07/360,386, filed Jun. 2, 1989, now U.S. Pat. No. 5,043,261.

FIELD OF THE INVENTION

The present invention is directed to a method for freezing, including freeze-drying, cells or cell-like materials. In particular, the invention is directed to a method for freezing platelets for storage.

BACKGROUND OF THE INVENTION

Current storage of fresh human platelets in liquid form (i.e., as platelet-rich concentrate in residual plasma) is limited in the following ways:

1) Platelets in liquid suspension (platelet concentrate) are generally not stored refrigerated as they suffer from a well-documented "storage lesion" involving loss of clotting function and in vivo viability (refer to AABB Technical Manual, 10th edition, 1990, pp.51–52). Platelet concentrates stored refrigerated are limited to a 72 hour shelf life due to the rapidity of the storage decay. The method used by most blood banks is to store platelet concentrate at room temperature (20–24 deg. C.) with continuous agitation by mechanical rocking. Agitation is essential at these temperatures to prevent cell aggregate formation. Currently regulations of the U.S. Food and Drug Administration (FDA) limit room temperature storage to 5 days.

2) The quality of room temperature stored platelet concentrates, as measured by aggregometry and other in vitro measures, decays after the first 24 hours of storage to some 75–85% of fresh values. Further deterioration occurs by five days of storage, such that the therapeutic value is only about 30% of fresh cells (i.e., the clotting efficacy of infused 5 day-old concentrate in patients, as measured by their bleeding time reduction, is only some 30% of a comparable dose of fresh platelets).

3) FDA limits room temperature storage of platelet concentrates to five days due to the threat of bacterial growth in the nutrient rich plasma concentrate. Contamination of platelet concentrates by Yersinia bacteria has been associated with deaths due to platelet transfusion.

4) The short shelf life means that some 25% of platelet concentrates collected by U.S. blood banks become unusable by outdating. This is a loss of a valuable voluntary resource.

The current useful method of storage of platelet concentrates in frozen form uses a 5% DMSO storage method developed by Schiffer et al (1983) Annals N.Y. Acad. Sci. 411, 161–169. This requires that the cells be stored at −120 deg. C. in the vapor phase of liquid nitrogen. Most blood banks do not use this method due to the expense of liquid nitrogen storage, plus the impracticality of shipping in liquid nitrogen. (See AABB Technical Manual, 1990, pp. 100–101 for review of blood cell freezing literature). Valeri has reported a 6% DMSO method that allows storage at temperatures as high as −65 deg. C., (referenced in the AABB Manual p. 102), a temperature compatible with ultra-low mechanical freezers. These freezers are also very expensive and have limited storage capacity.

An accepted shelf life for frozen platelets in 5% DMSO is 3 years. In actual clinical use, a frozen-thawed DMSO unit of platelets will normally exhibit about 50–60% of the clotting efficacy seen with a fresh platelet concentrate unit (i.e., usually two units of frozen thawed platelets are needed to achieve the same effect in vivo as one fresh unit).

It should be noted that FDA has not approved any DMSO platelet frozen storage method due to controversy over the efficacy and possible toxicity of DMSO (usually the frozen cells are thawed and infused directly, along with the 5% DMSO). Thus, U.S. blood banks today only freeze and infuse platelets with the approval of their medical review boards (i.e., interstate transport is prohibited).

Platelets are collected at most blood collection facilities, ranging from large regional blood centers (over 100,000 donations per year) to local hospital blood banks. Platelets can only be stored for 5 days as a platelet-rich plasma fraction at room temperature according to current FDA regulations. Although platelets can be frozen at −80 degrees for up to two years, the expense of freezing has discouraged frozen storage among civilian entities. The short shelf life is a major impediment to directed pre-deposit of plateletpheresis units.

A second issue problem is the transport of frozen platelets, which presents difficulties in container design, especially for air shipment. There is thus a need for lyophilized platelets which can be stored, shipped and reconstituted for therapeutic use.

Platelets play a vital role in blood clot formation and platelet transfusions are administered to arrest an existing bleeding condition or to prevent an imminent loss of blood. Often platelet transfusions are indicated when the patient cannot mobilize his own platelet reserves, as a result of standard chemotherapy treatments or diseases that cause low levels of circulating platelets or loss of normal platelet function. The American Red Cross (ARC) in 1987 reported a total of 4,500,000 transfusions of random donor platelet units and 350,000 transfusions of plateletpheresis units during calendar year 1986 in the United States. Some 245,000 patients received platelet transfusions during this period. The average patient receiving random donor units isolated from whole blood donations required 6 platelet units per transfusion event and also required 6 separate transfusions per year. The high rate of transfusions reflects the need for multiple transfusions for cancer patients undergoing aggressive chemotherapy or bone marrow transplantation as an adjunct to chemotherapy.

Multiple platelet transfusions can cause immune sensitization and rejection, especially when random donor units are used. This sensitization reaction, combined with improved plateletpheresis methods, has spurred demand for directed-donor plateletpheresis units. Plateletpheresis selectively isolates platelets from whole blood and returns the depleted blood to the donor's arm. This allows collection of concentrated platelet units from a single donor, as often as once per week. Each plateletpheresis unit contains the equivalent of 5–6 units obtained from donated whole blood (random donor units). Plateletpheresis allows more closely matched donors, such as close relatives, to donate and minimize the risk of sensitization. The use of concentrated plateletpheresis units also reduces the patient's exposure to numerous random donors, which reduces both sensitization risk and exposure to viral contaminants (a chemotherapy patient may require 60 platelet units during the course of treatment, and may be exposed to over 50 random donors).

Platelets are prescribed to control massive bleeding events before or during cardiopulmonary bypass surgery, and organ transplants. Unlike red cells, the normal human body possesses platelet reserves that can be mobilized rapidly if blood is lost. As a result, the U.S. Department of Health and Human Services advises that platelets not be wasted on prophylactic transfusions for routine surgery or even most trauma situations (patients can cope with a major bleed of 20 units by mobilizing platelets provided red blood cells are administered).

Bone marrow transplants designed to restore marrow destroyed by chemotherapy accounts for the single most intensive use of platelet transfusions. Most patients recovering from chemotherapy require at least three weeks (and sometimes months) before the new bone marrow graft can begin to produce platelets. During this period circulating platelet levels are maintained by transfusions, which must be frequent due to the short 5 day circulation lifetime of normal platelets.

The present invention provides a method utilizing a buffer for platelets which allows frozen storage at high temperatures (i.e., in the range of −20 deg. C.). This temperature range is easily achieved by conventional mechanical freezers such as chest freezers now used for food storage. The present invention enables long term frozen storage, which will obviate the short shelf life of room temperature or refrigerated storage, as well as the threat of bacterial growth in room temperature stored liquid concentrates. The prohibitive costs of liquid nitrogen frozen storage or ultra-low temperature mechanical freezers are also eliminated, and the use of DMSO is eliminated.

The present invention provides a method for freezing (and freeze-drying) cells or cell-like materials, including platelets, by the use of polymer glass transition theory to determine an effective cryopreservation for natural cells suspended in an aqueous environment. As reviewed by Levine and Slade (1987) Water Science Reviews (F. Franks, ed.) Vol. 3, pp. 79–185, Cambridge University Press, in aqueous systems comprising many natural and synthetic polymers, water acts as a plasticizer that affects the glass-to-rubber transition temperatures (Tg') of the aqueous-polymer system. This area of research has had a significant impact on the design of polymeric food materials (such as those based on starches), since the raising or lowering of Tg' can confer unique advantages for processing or storage stability of a material.

A working definition of a glass (Levine and Slade, 1987) is that it comprises a mechanical solid capable of resisting flow. In a typical amorphous glass the viscosity is extremely high, in the range of $10^{11}$ to $10^{14}$ Pa-s at the glass transition temperature (Tg). The Tg value, as illustrated in FIG. 2.4 of Slade and Levine (1987) occurs at the transition from the glassy fluid to the rubbery fluid state for systems comprising glassy or partially crystalline polymers. Below Tg, in the glass phase, the high viscosities preclude molecular diffusion and hence chemical reactions (which can lead to product spoilage) cannot proceed at significant rates. From this same figure another important point can be seen: that once the product temperature exceeds Tg, viscous flow can occur in the rubbery state, allowing for molecular diffusion and chemical reaction rates to proceed with exponential kinetics (WLF kinetics).

As a practical example, this explains why certain frozen and perishable biological products, such as human blood cells, must be stored within carefully defined temperature ranges (American Association of Blood Banks Technical Manual, 10th edition, 1990, chapter 5, pp. 91–103). Currently accepted blood cell freezing solutions containing glycerol or dimethylsulfoxide (DMSO) form glasses at very low temperatures (between −65° C. and −198° C.), thereby maintaining the cells in a chemically unreactive environment. However, exposure to temperatures that exceed Tg lead to poor cell viability as measured by red blood cell circulation time following freeze-thawing and transfusion or bleeding time reduction following transfusion of frozen-thawed platelets. In essence, the perishable cells can spoil even at temperatures below 0° C. normally thought of as "freezing temperatures" because the cryoprotective media have Tg values much lower than the −20° C. range commonly achieved by standard kitchen freezers.

Many of the fundamental principles of glass transition theory have derived from physical chemical studies in single component systems (see Levine and Slade, 1987) capable of forming a homogeneous "pure" glassy phase at the glass transition temperature (Tg) characteristic of that component, and in multicomponent systems. The present invention, however, provides multi-component aqueous cryopreservative systems that at appropriate temperatures form partially crystalline mixtures of water ice with interspersed regions of a separate amorphous glass phase. As defined in Pikal (1990), BioPharm, September–October 1990, the glass transition temperature of the amorphous phase in a partially crystalline aqueous system will be defined as Tg', to distinguish this particular phase from the glass transition temperatures of individual buffer components (i.e., the component Tg values).

SUMMARY OF THE INVENTION

The present invention provides a method, and cryoprotective compositions for use therewith, for freezing, including freeze-drying, cells or cell-like materials. The cells and cell-like materials include eryothrocytes, platelets, cell-membranes, stem cells, lymphocytes, and the like. The invention provides cryoprotective compositions which protect the cells or cell-like materials during freezing, freeze-drying and/or storage and which permit these processes and storage to be performed at temperatures which do not require liquid nitrogen, potentially toxic materials such as DMSO, or expensive low temperature refrigeration equipment. Typically, according to the present invention, freezing or freeze-drying may be performed above about −45° C. to about room temperature, and storage conditions may be from −80° C. to 0° C. (for frozen cells or cell-like materials), or up to room temperature (for lyophilized cells or cell-like materials). Predetermined temperatures for freezing, freeze-drying and storage of the cells which allow for optimum cell characteristics or recovery and shelf-life may be obtained by utilization of cryoprotective compositions according to the invention.

The aqueous mixture of cells, cell membrane or cell-like materials will be characterized by a high glass transition temperature, usually above about −60° C., and will contain a cryoprotective component. This component will comprise one or more permeants, i.e., compounds capable of penetrating the cells or cell membranes. The cryoprotective components will also contain one or more impermeants, i.e., compounds impermeable to the cells or cell membranes, wherein the amount of impermeants present in the mixture is a weight fraction sufficient to overcome the predicted depression in the glass transition temperature of the mixture attributable to the permeants.

DESCRIPTION OF THE PREFERRED EMBODIMENTS

Among the polymeric food ingredients that have been studied by others are natural polymers such as gelatin, gluten, starches, and frozen aqueous solutions of small sugars (i.e., mono- and disaccharides), polyols (glycerol), and starch hydrolysis products. Synthetic polymers such as PVP (polyvinylpyrrolidone) and PVAc (polyvinylacetate) in water have also been studied. Each of these materials in aqueous solution can be considered as an amorphous or partially crystalline polymer system that is plasticized by water. Glass transition theory as applied to these partially crystalline water-polymer systems focuses on the critical variables of moisture content (or percent dryness), temperature, and time to predict and regulate the cryostabilization of frozen or freeze dried products. The present invention provides aqueous-polymer buffers for the cryostabilization of natural cells by application of these principles.

Figure 1:
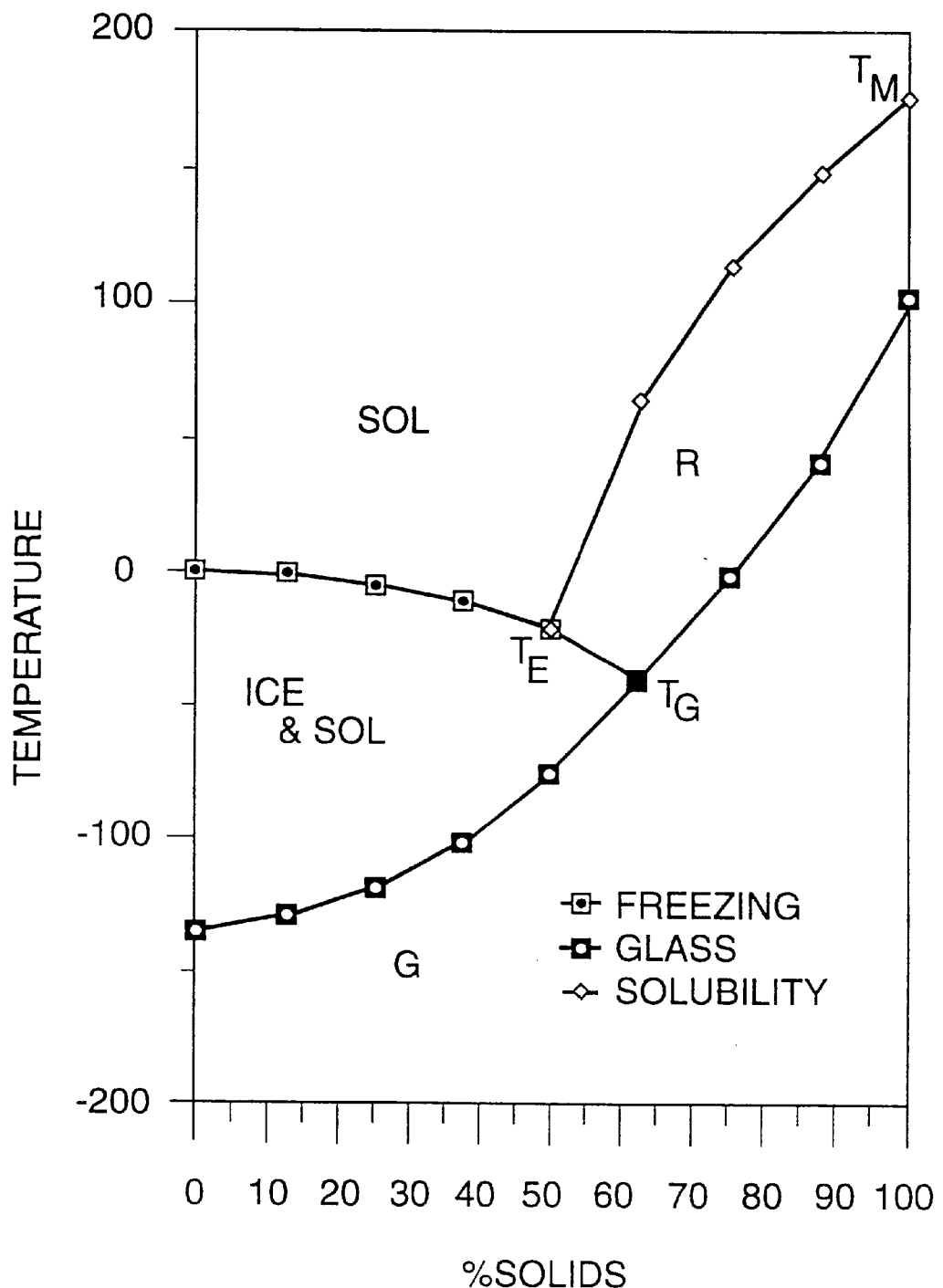
FIG. 1 is a phase diagram of an aqueous-polymer solution.

Referring to FIG. 1 an idealized phase diagram is shown for an aqueous-polymer solution comprising an amorphous, partially crystalline system, which illustrates the relationship between the moisture content (or percent solids) and temperature. The hypothetical system is characterized by distinct freezing and glass transition (Tg') curves that define different physical states: R=rubbery phase, SOL=solution phase, ICE/SOL=mixture of ice and solution, and G=glassy phase. The essential principle is that when the system is maintained at temperatures below the glass transition curve, an amorphous (noncrystalline) glass exists that is characterized by extremely high viscosities that prevent molecular diffusion on practical time scales. Thus, in the glassy state most chemical reactions such as degradative oxidation reactions that can damage cellular components, are inhibited. The slow kinetics of chemical reactions under these conditions lead to a cryostabilized product at the appropriate temperatures.

From FIG. 1 it can also be seen that Tg' increases most rapidly in aqueous glassy polymer systems of low moisture content. This is also expressed as a depression of Tg' by the plasticizing effect of increasing water content. PVP represents a typical water-soluble, glassy (non-crystallizable) polymer. Therefore, reduction of water content (i.e., by freeze-drying) is one approach to elevated temperature storage stability, as the resulting dried polymer composition has a higher glass transition temperature. It can be seen from our hypothetical curve in FIG. 1 for a water-PVP system, that the Tg' can exceed 0 degrees Celsius at sufficiently low moisture content. This indicates that prolonged storage at above freezing temperatures can be achieved under the proper conditions.

It is known that Tg for a pure polymer varies with the polymer weight average molecular weight: Tg increases with increasing average molecular weight, up to a limiting molecular weight value. The greatest increase in glass transition temperature is seen at low moisture contents (i.e., high weight percent of polymer). Thus, selection of water-soluble polymers of increasing average molecular weight to incorporate into an aqueous cryostabilizing buffer can further elevate the Tg' of the amorphous phase, due to the increased Tg of the individual polymer component. The relative contribution of each polymer component to the overall Tg' increases as the weight percent of that component in the aqueous solution increases.

Furthermore, by increasing the weight fraction of starch, or conversely increasing the weight fraction of water will respectively increase or depress the Tg' of the system. It can thus be extrapolated that more refined control of the Tg' value for a particular aqueous cryostabilizing buffer system can be attained by adding to pure water (which has a tg of −135° C.) multiple solute components of differing molecular weights (and hence higher or lower component Tg values) in appropriate weight percentages.

According to the invention these considerations of individual component Tg values and the weight percent of each component in an aqueous are utilized to provide multicomponent buffer formulations that have elevated (above −45° C.) Tg' values. The calculated buffer Tg' values, based on known component Tg values and their weight percent in a particular buffer formulation, allow accurate predictions of the buffer Tg'.

For freeze-drying a cryostabilizing buffer must have a Tg' that is appreciably above −45° C., since the product cannot be kept frozen at lower temperatures if efficient sublimation is to occur. Below this temperature the vapor pressure of water is so low that even under high vacuums of 100 mTorr or less achieved in conventional freeze-drying equipment the rate of sublimation is too low to be practical.

The phenomenon of freeze concentration during the freezing process is another consideration. In aqueous systems containing dissolved solutes, the initial freezing event involves conversion of liquid water to crystalline ice. The dissolved solutes are thereby concentrated out of the ice phase into a residual liquid phase in which the concentration of dissolved solutes increases significantly. At sufficiently low temperatures, below Tg', this non-crystalline phase becomes a glass. Implicit in this description is the fact that valuable components such as proteins or blood cells also become concentrated into the glassy phase. The high electrolyte and buffer concentrations in this phase can be damaging to proteins or cellular membranes. Hence, it is preferable to start with the minimal acceptable concentrations of salts and buffering agents (buffered phosphate), as these will become further concentrated during freezing into the same amorphous phase that contains the product of interest.

The process of lyophilization by sublimation is defined as removal of water vapor directly from the ice phase. During lyophilization the ice crystals are removed by sublimation, leaving open pores or channels in the frozen, partly dried matrix. Formation of these channels is critical for thorough primary drying (in which the bulk of the water is removed as water vapor from the ice phase), as these channels allow water vapor to escape from regions below the surface of the product "cake". During primary drying the product should be maintained below the collapse temperature, which is usually identical to the Tg' of the amorphous glass phase containing regions of maximally concentrated solutes. If the product temperature exceeds Tg' during primary drying, then regions of amorphous glass will have sufficient fluidity to undergo viscous flow once the ice is sublimed, thereby blocking the open channels and preventing further sublimation. Thus, it can be seen that cryostabilizing buffers must first achieve a measurable and elevated Tg' value that will allow the material to be held below Tg' during ice sublimation.

Once the bulk of the water in the product is removed during primary drying, the secondary drying phyase begins. During secondary drying, the residual moisture in the amorphous phase is removed by evaporative or vacuum drying. Evaporative drying involves removal of water vapor from the nonicy state.

The accepted methods for frozen storage of human blood cells (red cells, platelets, stem cells and lymphocytes) generally involve aqueous glycerol or DMSO solutions. Both of these compounds have very low glass transition temperatures (Tg values), such that the current formulations for cell freezing (40% w/v glycerol or 5% v/v DMSO; see the AABB Technical Manual, 1990) have low glass transition temperatures that are below about −65° C. (in these systems the aqueous solution is referred to as having a Tg value, since the term Tg' is meant to specify glass transition temperature in a partially crystalline system). In addition, both glycerol and DMSO are potent chaotropic agents that prevent the formation of crystalline ice in aqueous solutions when present in the amounts currently used. Although this prevents ice crystal damage to cells during frozen storage at ultralow temperatures, the requirement of ice channel formation during freeze-drying suggests that these cryoprotectant formulations are not useful for freeze-drying by sublimation, or for freeze-evaporative drying because of the need for very low frozen temperatures at which teh vapor pressure of water is very low. This also explains the empirical findings reviewed in the AABB Technical Manual (1990), chapter 5, that cells stored frozen in either of these solutions lose their functional viability if the storage temperature exceeds −65° C. for the high glycerol solution, or −120° C. for the DMSO solution: frozen storage at temperatures that exceed Tg lead to a glass-to-rubber transition in which viscous flow occurs in the rubbery state, allowing for molecular diffusion and degradative chemical reactions to proceed at appreciable rates. Neither the existing 40% glycerol system or the DMSO system are useful for high temperature frozen storage (in the range of −20° C.), but this temperature range is a necessity for efficient lyophilization.

The present invention provides aqueous buffer solutions for cryostabilization of cells and cell-like materials that comprise buffers having elevated glass transition temperatures (Tg'). The higher the glass transition temperature for a particular aqueous suspension of biological cells in a buffered polymer mixture, the higher the useful storage temperature. From FIG. 1 it can be seen that the glass transition curve for any aqueous polymer system depends upon the weight fraction of total solids in the solution. Based on the foregoing discussion, the following considerations should be used in the selection of an aqueous cryostabilizing buffer system according to the invention for maintaining perishable biological materials, such as cells or proteins, in a stable frozen state (either for frozen storage or during a freeze-drying procedure):

1) The buffer should have the highest practical glass transition curve (Tg'), with a minimal component of salts or buffering agents that may contribute to freeze-concentrate damage.

2) The overall glass transition temperature of a particular aqueous buffer system will depend on the glass transition temperatures of each of the individual solutes and upon their respective weight fraction in the mixture. This relationship can be approximated by the following:

Equation 1

$$Tg'(\text{buffer}) = (TgA)(Wt.\ \% A) + (TgB) \ldots + (Wt.\ \% B) + (TgN)(Wt.\ \% N) - 5.2°\ C.$$

where Tg' (buffer) is the glass transition temperature of the total solution; 'Tg A is the glass transition temperature of solute A; Wt. % A is the weight fraction percent of solute A in the buffer; N is the last member of N components; and 5.2° C. is an empirically derived value to correct for volume displacement of the solid components in the solution.

3) For use with biological or artificial membrane systems (i.e., cells or liposomes), the buffer should contain permeant cryoprotectant agents capable of penetrating the phospholipid bilayer of the membrane to stabilize the internal lipid bilayer, and also to stabilize intracellular or intravesicle components (organelles, internal membranes, enzymes, etc.). Useful membrane-permeants include small sugars, such as monosaccharides, and polyalcohols (polyols) such as glycerol or polypropylene glycol. These small sugars and polyols generally have low individual glass transition temperatures, and their inclusion in a buffering system will lower the overall Tg' of the solution proportional to their weight fraction in the solution, as described in Equation 1 above. These same polyhydroxy compounds also serve as water replacement agents as suggested by Crowe (Bio Chem. Biophys. Acta, 939, 327–334 (1988)), to produce the structure of cell components, such aS the phospholipid bilayer.

4) To achieve elevated glass transition temperatures for aqueous buffers comprising membrane permeant small sugars and/or polyols, one or more water soluble polymers must be included in sufficient weight fraction percentages to overcome the Tg-depression caused by the cell permeant components. Use of higher average molecular weight polymers is helpful as Tg for an amorphous polymer increases with molecular weight. These high molecular weight polymers can comprise natural (starches, gelatins, etc. derived from plant, animal or microbial sources) or synthetic (PVP) polymers, or mixtures of polymers of various average molecular weights.

5) For use in transfusion medicine, the components of the aqueous buffer system must also be biocompatible, nontoxic, and available as sterile, pyrogen-free materials.

Using Equation 1 above, buffers are provided based on the calculated glass transition temperature, as shown, for example, in Table 1. Equation 1 shows that control over the Tg' of an aqueous cryostabilizing buffer system can be achieved by exploiting the glass transition temperature characteristic of each individual buffer component and its weight fraction in the buffer solution.

Preferred impermeant compounds include amorphous and/or partially crystalline polymers or mixtures thereof. These may be natural or synthetic polymers, preferably of molecular weight over about 300, and most preferably about 10,000–500,000. The polymers are preferably present in the solution in weight percentages from about 1% to their limit of solubility. Preferred weight fractions are 5%–25%.

Preferred permeant compounds include carbohydrates, preferably monosaccharides, disaccharides or mixtures thereof. Typically each of the permeants will be present in a weight fraction from about 0.01% to their respective solubility limits. Preferred weight fractiosn are from about 0.5% to 20%.

The preferred monsaccharrides are 6•carbon hexose sugars and 5•carbon pentose sugars. Preferred disaccharides are maltose, lactose, sucrose, trehalose.

Polyalcohols may also be used as permeants, preferably in concentrations of 0.1% to 40% by volume, and most preferably in the range of 5%–25%.

In Table I below, the reported glass transition temperatures for a series of useful buffer components are shown. These values are reported in Slade and Levine (1987), pp. 112–115.

TABLE I

REPORTED GLASS TRANSITION TEMPERATURE VALUES

| Starch Hydrolysis Products | Manufacturer | Tg' (deg. C.) |
|---|---|---|
| Paselli MD-10 (potato) | AVEBE | -8 |
| Paselli SA-10 (potato) | AVEBE | -9.5 |
| Maltrin M150 (corn) | GPC | -13.5 |

| Polyalcohols | Molec. Wt. | Tg' (deg. C.) |
|---|---|---|
| ethylene glycol | 62.1 | -85 |
| 1,3-butanediol | 90.1 | -63.5 |
| glycerol | 92.1 | -65@ |

| Sugars (Mono/Di saccharides) | Molec. Wt. | Tg' (deg. C.) |
|---|---|---|
| xylose | 150.1 | -48 |
| ribose | 150.1 | -47 |
| glucose | 180.2 | -43 |
| fructose | 180.2 | -42 |
| galactose | 180.2 | -41.5 |
| mannose | 180.2 | -41 |
| sucrose | 342.3 | -32 |
| maltose | 342.3 | -29.5 |
| trehalose | 342.3 | -29.5 |
| lactose | 342.3 | -28 |

| Polymers | Approx. Average MW | Tg' (deg. C.)* |
|---|---|---|
| PEG | 300 | -63.5 |
| gelatin | N.D. | -8 |
| dextran | 9,400 | -13.5 |
| hydroxyethyl starch (HES) | N.D. | -6.5[1] |
| PVP-10 | 10,000 | -26 |
| PVP-40 | 40,000 | -20.5 |

PEG = polyethylene glycol
PVP = polyvinylpyrrolidone
Pure water has an estimated Tg of -135° C.
*The reported polymer Tg values in Slade and Levine (1987), p. 131, are compiled from literature values (the value for gelatin is based on collapse temperature during freeze-drying).

TABLE I-continued

REPORTED GLASS TRANSITION TEMPERATURE VALUES

[1]No average molecular weight value is reported in Slade and Levine for HES, and this value will vary depending on the average MW (HES is available in a range of molecular weights, up to about 500,000).
@Pure glycerol has a Tg of -95° C.

From the representative Tg' values presented in Table I, it and the teachings herein on these kinds of components, added in different weight fraction proportions, can be used to control the final Tg' of an aqueous buffered medium. Use of multicomponent buffers containing low molecular weight, membrane permeable molecules (polyalcohols and monosaccharides) are vital for preservation of intracellular structures. As seen from Table I, these small molecules have low individual Tg' values, and if present in large concentrations would lead to excessively low buffer Tg' values (i.e., the accepted 40% glycerol medium for freezing red cells has a low glass transition due to the -65° C. glass transition of the glycerol component). Thus, these small molecules should preferably be used in low concentrations if a high Tg' buffer is desired. In addition, these small molecules can be formulated in combination with one or more polymers of varying average molecular weights to raise the overall Tg' of the buffer. By these strategies a suitable cellular cryostabilizing buffer for use under a range of freezing temperatures (and ambient temperatures in the freeze-drying process) can be formulated.

Other buffer parameters, such as potential cell toxicity, cell aggregation behavior, or cellular cryostabilizing efficacy, under the desired freezing or freeze-drying conditions may also be considered in selecting components of the buffer. Different buffer components may be required for specific mammalian cell types; for example, in the present invention we show that glycerol is amenable to human red blood cell cryopreservation, but is not as efficacious with human platelets. Hence the method of the present invention focuses buffer design in terms of the physical-chemical requirements of freezing or freeze-drying, but each mammalian or other cell type may have special requirements based on its unique differentiated properties (i.e., the need to preserve oxyhemoglobin in mature red blood cells or the need to preserve nuclear structures in nucleated cells).

Figure 2:
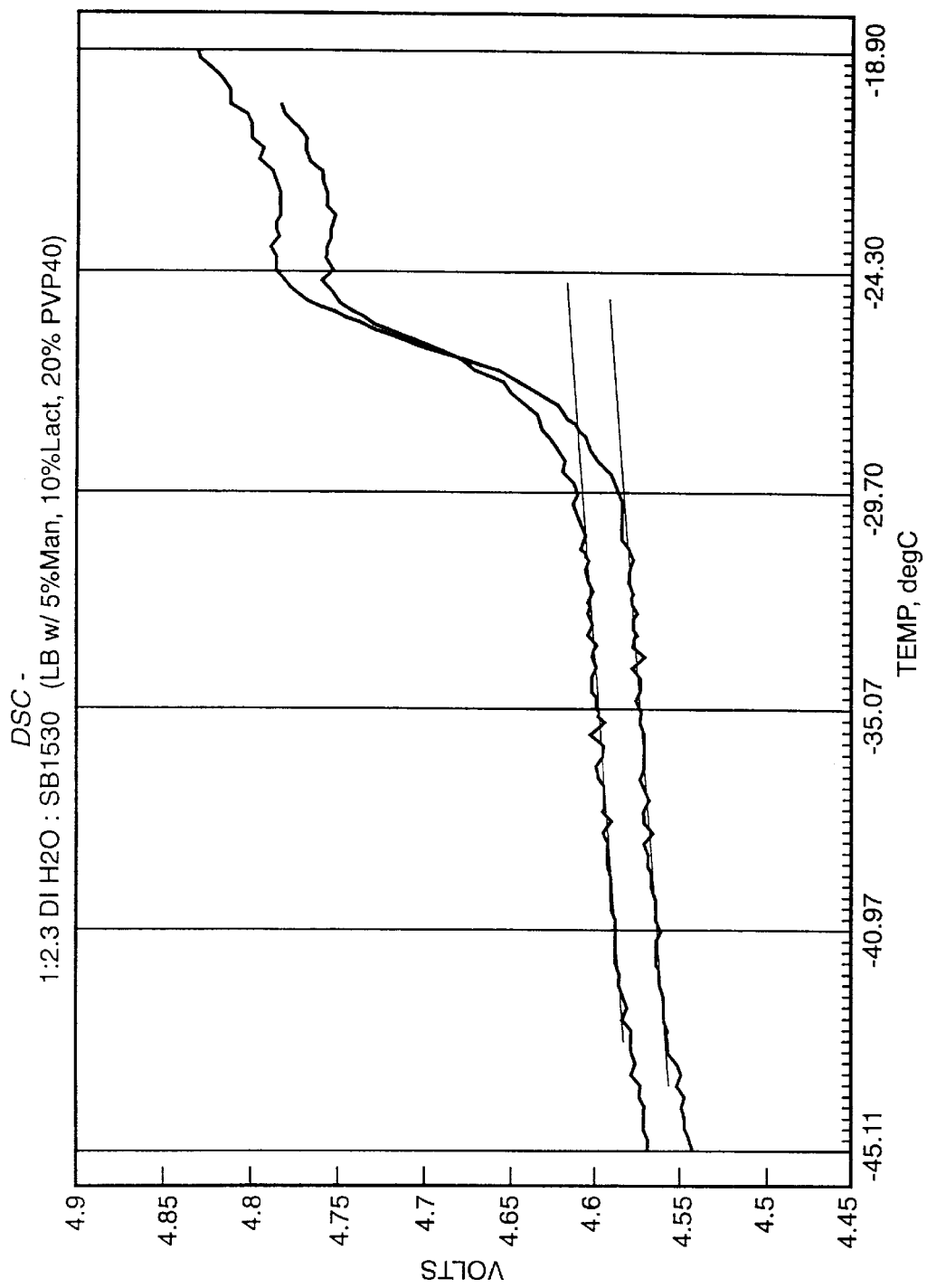
FIG. 2 is the profile of a DSC thermal analysis of a buffer described in Example 1.

The calculated buffer Tg' value can be directly compared to the measured value determined by thermal analysis by differential scanning calorimetry (DSC) analysis. A representative DSC profile for one aqueous buffer formulation is shown in FIG. 2, for a three component buffer containing as its principle weight fraction components 5% mannose/10% lactose/20% PVP-40,000 MW (trace buffer salts are present but are ignored for the purpose of calculating Tg' as their contribution is minimal). The calculated Tg' derived from Equation 1 for this formulation is -30.7° C., and in FIG. 2 the DSC traces for two sample runs show the measured values to be -30.0° C. and -30.25° C. These values are in excellent agreement with the calculated Tg' value. It should be noted that in practice this cryostabilizing buffer was diluted in the ratio 2.3 parts buffer: 1 part cell suspension, so in FIG. 2 the DSC analysis was performed on a 2.3:1 mixture of buffer:water to approximate final concentrations in actual use.

It will be understood that the buffers according to the present invention may also contain basic salts compatible with the biological material. Such salts include electrolytes, cofactors, metal cations, metabolites, buffer salts, vitamins, hormones, growth factors, and the like. The cells, cell-membranes and cell-like materials which may be treated according to the present invention include mammalian cells (including human), tissues, peripheral blood cells (red blood cells, platelets, stem cells, leucocytes), mammalian cell membranes, including membranes of periferal blood cells.

From the foregoing description one of ordinary skill in the art may formulate cryostabilizing buffers for use in frozen storage or for use in freeze-drying of perishable biological cells or proteins.

EXAMPLES

Example 1

For frozen storage stability, we formulated several three component buffers listed in Table 2, following the main requirements: 1) the buffer must include at least one membrane permeant cryoprotectant, selected from available monosaccharides that can traverse phospholipid bilayers (polyacohols may also be used); 2) the buffer may include a membrane impermeant cryoprotectant, usually a disaccharide or higher molecular weight carbohydrate or polymer; 3) at least one polymer must be present in sufficient weight percentage and having sufficiently high average molecular weight (hence high Tg) to boost the glass transition temperature (Tg') of the buffer solution; and 4) the relative weight percentages of the individual buffer solutes must be adjusted so that the calculated Tg' exceeds $-45°$ C., and preferably for convenient frozen storage, is above $-25°$ C. (buffers prepared to have a calculated Tg' are then measured by DSC analysis to confirm the actual Tg' at final buffer concentrations contemplated for use with cell suspensions); 5) the use of polyhydroxy components (monosaccharides, disaccharides, polyalcohols, starches) contributes to membrane stabililzation by water replacement.

In FIG. 2 we show a typical DSC thermal analysis profile obtained from a sample of buffer #1(5% mannose/10% lactose/20% PVP-40) in Table 2. The buffer:water mixture exhibits a characteristic and reproducible inflection point at the Tg' onset temperature. By use of DSC analysis, the calculated Tg' for any known aqueous buffer formulation may be confirmed. In addition, DSC analysis can be used to uniquely identify and characterize a buffer formulation in terms of its measured Tg'. This same kind of analysis can also be applied to mixtures of buffer and biological cells.

Example 2

In Table 3 we predict the Tg' of a multicomponent mixture. By varying the individual components along the theme of monosaccharide/disaccharide/polymer, buffers are formulated with actual Tg' values measured by DSC analysis that correspond closely to the calculated value. Furthermore, by varying the individual component weight fractions in the solution (expressed as a w/v percent), and selecting polymers of desired average molecular weight, it is possible to design buffers that have a range of Tg' values within the useful temperature limits of $-45°$ C. to $0°$ C. It should be noted that the measured Tg' values in Table 3 are for 2.3:1 dilutions of buffer: water to mimic mixing the buffer with an aqueous suspension of cells. Furthermore, in a freeze-drying application (where water is removed from the system by either sublimation or evaporation), the starting Tg' will increase as the moisture content is reduced. Thus, although these buffers all have starting Tg' values in the range of $-33.5°$ C. to $-21.25°$ C., the final dried product will have a Tg' considerably above these measured starting values. It is the final Tg' of the dried product that will determine the storage temperature limit for the dry material.

Example 3

In FIG. 1 we described a hypothetical aqueous, partially crystalline system to illustrate the prediction from glass transition theory that the glass transition temperature of the amorphous phase (Tg') should rise as residual moisture decreases (or as % solids increases). From FIG. 1 it can also be expected that the rise in Tg' is most rapid at low residual moisture levels (i.e., at about 10% residual moisture or less). In this example we demonstrate the practice of this concept with an aqueous suspension of human red blood cells and a mixture of cryoprotectants, which is first frozen and then lyophilized to reduce the moisture content.

Packed human red blood cells were mixed in a 1:1.6 ratio by volume (1 part cells:1.6 parts buffer) with a cryostabilizing aqueous buffer comprising the following components:

1.7 M glucose

15% (w/v) hydroxyethyl starch, 500,000 $MW_{av}$

3% (w/v) polyvinylpyrrolidone, 360,000 $MW_{av}$

Basic Buffer Salts (see Table 1).

The resulting mixture of red blood cells and cryoprotective buffers was analyzed by differential scanning calorimetry, and the onset of the Tg' transition for this mixture was observed to occur at about $-38°$ C. The red blood cell and buffer mixture was then spread in thin layers in several Petri dishes and frozen at $-40°$ C. on the shelf of a Virtis lyophilizer (thin films were prepared to minimize temperature gradients that might form within thicker samples). After complete freezing, the samples were lyophilized at a constant shelf temperature of $-38°$ C. and pressure of 75 mTorr. At various time points separate samples were removed and weighed to determine the percent weight loss, from which it is possible to estimate the residual moisture content (the solids used to prepare the buffer are nonvolatile, so weight loss directly reflects the extent of removal of water vapor). The partially dried samples were also analyzed by differential scanning calorimetry to determine their glass transition temperature.

Figure 4:
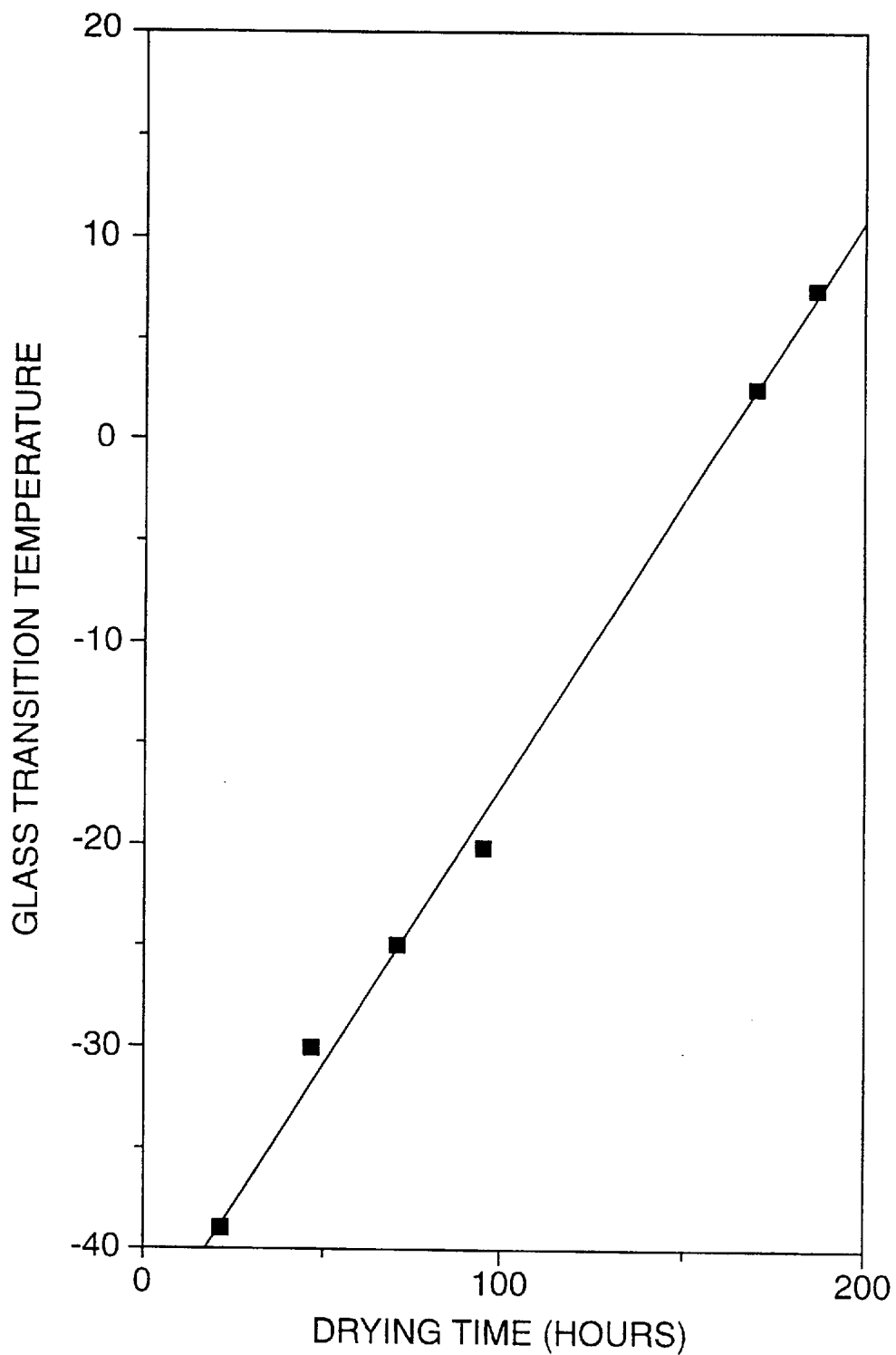
FIG. 4 is a plot to glass transition temperature as a function of drying time of a buffered red blood cell mixture described in Example 3.
Figure 5:
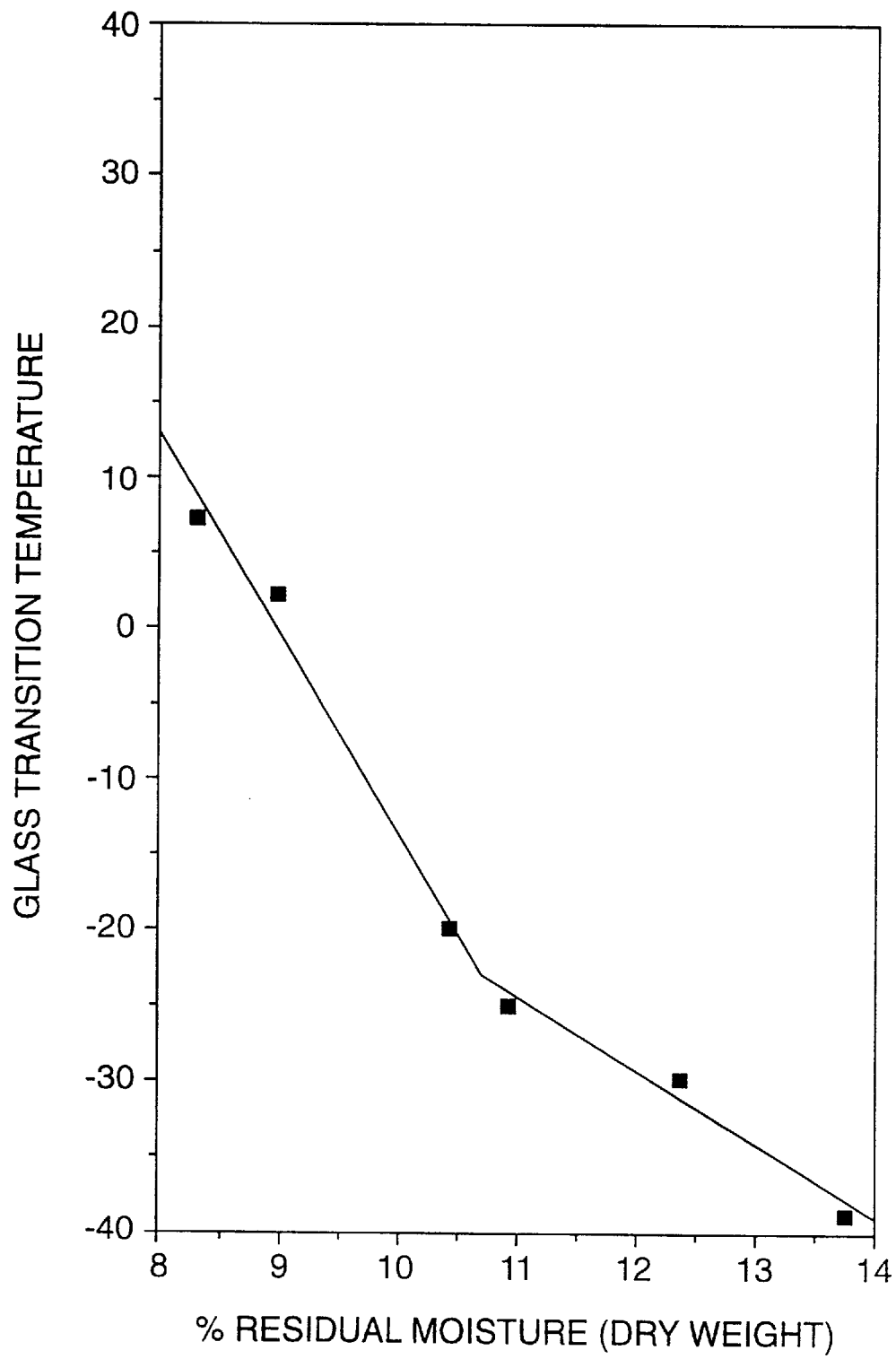
FIG. 5 is a plot of glass transition temperature as a function of residual moisture of a buffered red blood cell mixture described in Example 3.

The results are shown in FIGS. 4–5. As expected, the sample Tg' increased with longer drying times, in a linear relationship (FIG. 4). The drying cycle was stopped in this study after about 180 hours, at which time the sample glass transition temperature had risen to between $+2°$ C. to $+7°$ C. In FIG. 5 our parallel weight loss measurements show that this rise in sample Tg' follows the loss of water vapor, as predicted by glass transition theory. As expected from the example in FIG. 1, we observed a change in the rate of Tg' increase when the sample reached about 11% residual moisture (i.e., the slope of the curve changes). This confirmed our expectations that an incremental reduction in residual moisture at low moisture contents leads to a larger increase in the sample Tg'. Thus we expect that the residual moisture content of mixtures of biological cells and cryostablizing compounds can be used to determine the product storage temperature and shelf life. The greatest advantage for ambient temperature storage will likely occur at low residual moisture content (i.e., at about 10% residual moisture or less).

This example illustrates the application of glass transition temperature theory to preservation of biological cells.

Example 4

Several of the buffer formulations listed in Tables 1–3 were used as cryoprotectants with fresh human red blood cells. Refrigerated packed red blood cells isolated from whole human blood collected in standard citrate-based anticoagulant were obtained from a blood bank. The cells were washed in dextrose-saline to remove the storage solution, and then 5 ml of washed red cells were mixed with 5.7 ml of each buffer (all concentrations in Tables 1–3 are for the manufactured buffers, prior to mixing with cells). An additional 5.75 ml of each buffer was then added, with additional mixing. The buffer/red cell mixtures were then frozen rapidly in a −80° C. ethanol bath, and the frozen samples stored 24 hours at either −80° C. or −38° C. Frozen samples were thawed in a 40° C. water bath with agitation, and washed in a series of reconstitution buffers designed to return the cells to isotonic conditions with minimal osmotic shock, and to remove any lysed cell debris. The thawed and washed cell suspensions were then subjected to analysis.

The post-thaw reconstitution procedure was performed on each sample as follows:

1) Thawed red cells were removed from the 40° C. water bath and 10 ml of 37° C. reconstitution buffer (2000 mOsmol) was added. After addition of the first 10 ml, another 10 ml of 2000 mOsmol buffer was added to the cells. The reconstitution buffers used in this procedure are based on a basic 300 mOsmol buffer recipe:

19% (w/v) PVP-10,000 MW
5 mM ATP
1.47 mM monobasic potassium phosphate
8.1 mM dibasic sodium phosphate
adjusted to pH 7.2

The above basic 300 mOsmol recipe was adjusted to either 2000 mOsmol or 1400 mOsmol by addition of potassium phosphate.

2) After mixing-in the 2000 mOsmol buffer, the cells were further diluted by sequentially adding two 10 ml aliquots of a 1400 mOsmol reconstitution buffer (prepared according to the basic recipe above).

3) At this step a 200 microliter sample of cells is removed for measurement of cellular hemoglobin recovery (this data is presented in Tables 4–6 as the Cell Recovery at Reconstitution).

4) The remaining red cell suspension is centrifuged at 1500 xg for 5 minutes, and the supernatant discarded. The cell pellet is then suspended in 10 ml 1400 mOsmol buffer, and then another 10 ml of 1400 mOsmol buffer is added. This suspension is further diluted with two serial 10 ml aliquots of the basic 300 mOsmol buffer listed above, and the cells are again centrifuged and the supernatant discarded.

5) The final cell pellet is then suspended in two serial aliquots of the basic 300 mOsmol buffer containing PVP-10,000 MW. To this suspension two serial 10 ml aliquots of the following buffer are added to complete the osmotic step-down of the cells to isotonic conditions:

10% (w/v) PVP-2500 MW
213 mM NaCl
5 mM dibasic sodium phosphate
5% glucose
pH 7.2 and 300 mOsmol The remaining analyses shown in Tables 4–6 are performed on this final cell suspension.

The following in vitro parameters were measured for each sample:

1) Cell recovery at reconstitution (step 3 of the reconstitution protocol), measured by the recovery of cellular hemoglobin using a spectrophotometric assay.
2) Overall cell recovery after reconstitution of the cells in 300 mOsmol PVP-2,500 MW buffer, again measured by hemoglobin retention in the final cell pellet.
3) Osmotic stability of recovered cells in physiological saline (weakened cells lyse upon incubation in saline, and the released hemoglobin can be measured in the supernatant).
4) Red cell indices: Mean Corpuscular Volume (MCV), Mean Corpuscular Hemoglobin (MCH), and Mean Corpscular Hemoglobin Concentration (MCHC) are obtained from a Serono-Baker hematology analyzer.
5) The recovery of functional hemoglobin is measured spectrophotometrically, and expressed as the percent of oxyhemoglobin, methemoglobin, and hemichromes present in the sample.
6) Red cell deformability (Dlmax) is measured by ektacytometry, which measures the extent of cell elasticity when subjected to a viscous shear stress. The Dlmax expresses the maximum deformability, and can be expressed as a percent of the control Dlmax observed with fresh red cells.
7) An osmoscan profile is obtained by combining the ektacytometry with a continuous osmotic solution gradient, to evaluate deformability under hypertonic and hypotonic conditions.
8) The Relative Filtration Index (RFI) measures the ability of cells to traverse a filter containing a 5 micron pore size (normal human red cells are about 2×5 microns in size). This mechanical barrier simulates circulatory stress encountered in the microvasculature.
9) Cell density is measured to assess the degree of cell swelling.

In Tables 4–6 we show the data obtained from freeze-thaw experiments in which human red cells were frozen and then stored at either −80° C. or −38° C. for 24 hours, and then thawed, reconstituted to isotonic conditions, and analyzed. The cryoprotectant buffers #1–9 are the same as those listed in Table 2. Duplicate cell samples (n=2) were evaluated for each buffer, and the mean values are reported in Tables 4–6. In each Table we also show the expected values obtained from fresh red cell samples analyzed as controls.

From the data in Tables 4–6 it can be seen that all of the freezing buffers tested confer significant cryostability to human red blood cells frozen and stored at −80° C., as measured by the percent of intact cells recovered at reconstitution. This protection extends to initial cell recoveries for those samples stored as high as −38° C. in the same buffer formulations. This result is consistent with the elevated calculated Tg' values (see Table 2) for these buffers. In addition, we noted that the PVP polymer based buffers in Table 2 offered the advantage that very little cell aggregation occurred after thawing, in contrast to some of the buffer formulations reported in Table 1 that use different polymer species (for example, fructose-dextran buffers were associated with cell aggregation, while fructose-PVP buffers exhibited no cell aggregation). Thus, although PVP and dextran can be used to elevate Tg', PVP is preferred since red cell aggregation is not observed after freeze-thawing in the presence of PVP.

The cryostabilizing properties of the buffers tested in Tables 4–6 at elevated temperatures of −38° C. suggest that high temperature frozen storage of human red cells can be achieved. In Tables 4–6 we observed that in general the reconstituted red cells showed reduced cell deformability and filterability (the Dlmax and RFI values, respectively). In addition, elevated hemichrome levels were observed, as though some hemoglobin oxidation had occurred. These observations suggested that a further refinement of the cell permeant (i.e., the monosaccharide component) of these buffers might lead to improved cellular cryostability at elevated frozen temperatures. In the next example we added a highly membrane permeable polyalcohol, glycerol, to our buffer formulations.

Example 5

The history of human red cell cryopreservation has focused on the use of either high glycerol alone (40% w/v solution), requiring frozen storage at −80° C., or use of low glycerol (20% w/v solution), requiring frozen storage at −120° C. in the vapor phase of liquid nitrogen. These very low storage temperatures are dictated by the low glass transition temperatures of aqueous glycerol solutions. From the principles of buffer design outlined herein, we have formulated low glycerol buffers containing carbohydrates and polymers that act as impermeant cryoprotectants that also elevate the Tg' to a temperature range above −45° C.

In Tables 7–9 we demonstrate the effect of using multi-component buffers containing glycerol or propanediol as a highly permeant cryoprotectant, in combination with small sugars and various polymers. In these experiments human red blood cells were mixed in a 1:3 volume ratio (cells:buffer) with a particular buffer formulation, and then frozen and stored at elevated freezing temperature (between −20° and −25° C.). About 5 ml of fresh starting packed red cells were used. The frozen cells were thawed and reconstituted by a series of dilutions to return them to isotonic conditions, according to the following protocol:

1) To the thawed cells two 5 ml aliquots of 2000 mOsmol reconstitution buffer (from Example 1) is added and mixed-in with the cells. This is followed by two 5 ml aliquots of 1400 mOsmol reconstitution buffer (Example 1) to yield a diluted cell suspension.

2) The diluted cells are recovered by centrifugation and the supernatant is discarded. The cell pellet is suspended in 5 ml 1400 mOsmol buffer, then diluted with another 3 ml of 1400 mOsmol buffer, then diluted again with two 5 ml aliquots of a 300 mOsmol dextrose-saline buffer (5% dextrose/0.9 % NaCl, w/v, adjusted to 300 mOsmol). At this point a 200 microliter sample is removed for the initial measurement of cell recovery, as in Example 1.

3) The cells are again pelleted by centrifugation and the supernatant discarded. The cells are suspended in 5 ml commercial dextrose-saline (Baxter Fenwal), and diluted with an additional 3 ml of commercial dextrose-saline. This final cell suspension is used for the remaining analyses in Tables 7–9.

The cell parameters measured in Tables 7–9 are as described in Example 1. In Table 7 we show the results of freezing red cells at high temperature (−22° C.) in a series of buffers containing 25% v/v glycerol in the initial buffer formulation (the starting buffer is diluted in the ratio of 1 volume packed red cells: 3 volumes buffer), so the final concentrations of buffer components in the frozen cell suspension is reduced. These conditions are also used in the experiments outlined in Tables 8 and 9.

In Tables 7–9 a significant improvement in the cell deformability (DImax), osmoscan trace relative to fresh cells, and cell filterability index (RFI) are observed over the data shown in the preceding Tables 4–6. We propose that the combined advantages of the highly permeant polyalcohols with permeant and impermeant carbohydrates (both monosaccharides and disaccharides) and polymers having high component Tg values, allows for the recovery of thawed reconstituted human red cells having excellent cell preservation qualities following frozen storage at temperatures as high as −22° C.

Example 6

In this example we extend the application of glass transition theory to freeze-drying of human red blood cells (freeze-drying can be achieved by direct sublimation, in which water vapor is removed from a frozen sample whose temperature is held under the Tg' of the composition, or also by evaporative drying, herein defined as removal of water vapor from samples having temperature above the Tg').

In Table 10 we explored the use of cryostabilizing buffers containing 25% (v/v) starting concentration of glycerol as the permeant cryoprotectant, in combination with various carbohydrates (both mono- and disaccharides) and polymers. In these buffers we focused on the application of hydroxyethylstarch (HES) as the polymer, having average molecular weights of 200,000 and 500,000 to elevate the buffer Tg' as predicted by glass transition theory. For comparison to the HES polymer (which has the added advantage of USP pharmaceutical grade), we examined several starch hydrolysis products prepared from natural starches (i.e., potato starch), commonly used in food product formulations. The starch hydrolysis products examined included SPG20 and Paselli MD10.

For these experiments the human red blood cells were mixed with each of the buffers listed in Table 10, frozen, and then subjected to freeze-drying at a starting freezedryer shelf temperature of −25° C. We use a Virtis shelf lyophilizer in this process. During the drying process the shelf temperature is ramped to +4° C. without causing sample fluidity. This is consistent with glass transition theory, as we expect the Tg' of the initially frozen composition to increase as water is removed during the freeze-drying. Hence the lyophilizer shelf temperature (and the sample temperature) can be raised as drying proceeds without causing sample fluidity and collapse. We monitored the amount of water removed from the samples by weight loss, and determined that in all cases at least 90% of the water initially present was removed (the solutes and cells being non-volatile). The dried samples were rehydrated and subjected to analysis as described in Tables 4–9.

In Table 10 each buffer formulation is designated by a number (i.e., SB 1965–SB 1978). The components of each aqueous system, in addition to the 25% v/v glycerol present in each are shown (all percentages are percent w/v). As a control, buffer SB 1965 contains only 25% glycerol in 40 mM phosphate buffer, pH 7.4 (all other buffers in Table 10 are made in 40 mM phosphate pH 7.4). As further controls, SB 1966 and SB 1967 contain 15% w/v SPG20 or 7.5% Paselli, respectively, which are hydrolysis products of natural starches.

From Table 10 it can be seen that SB 1909 in particular confers significant protection to the dried red blood cells, as seen from the high osmotic stability in saline (88.8% of the cells survive exposure to physiological saline), normal red cell indices (MCV, MCH, MCHC), and improved deformability (Dimax=92.6% of the value normally detected in fresh red cells). The filterability of these cells is also improved to some 50% of fresh red cell values. This sample was determined to have lost at least 90% of its moisture (i.e., contained 10% or less residual moisture) after drying. Buffer SB 1909 contains 25% (v/v) glycerol, 0.5% (w/v) glucose, 2.25% (w/v) lactose, and 7.25% (w/v) hydroxyethylstarch (HES-500 of 500,000 average molecular weight). This formulation illustrates the essential principles of the present invention: use of a highly membrane permeable component (glycerol), in combination with a membrane permeable monosaccharide (glucose), an impermeable disaccharide (lactose), and a high molecular weight polymer (HES) to elevate the Tg' of the multicomponent buffer.

Figure 3:
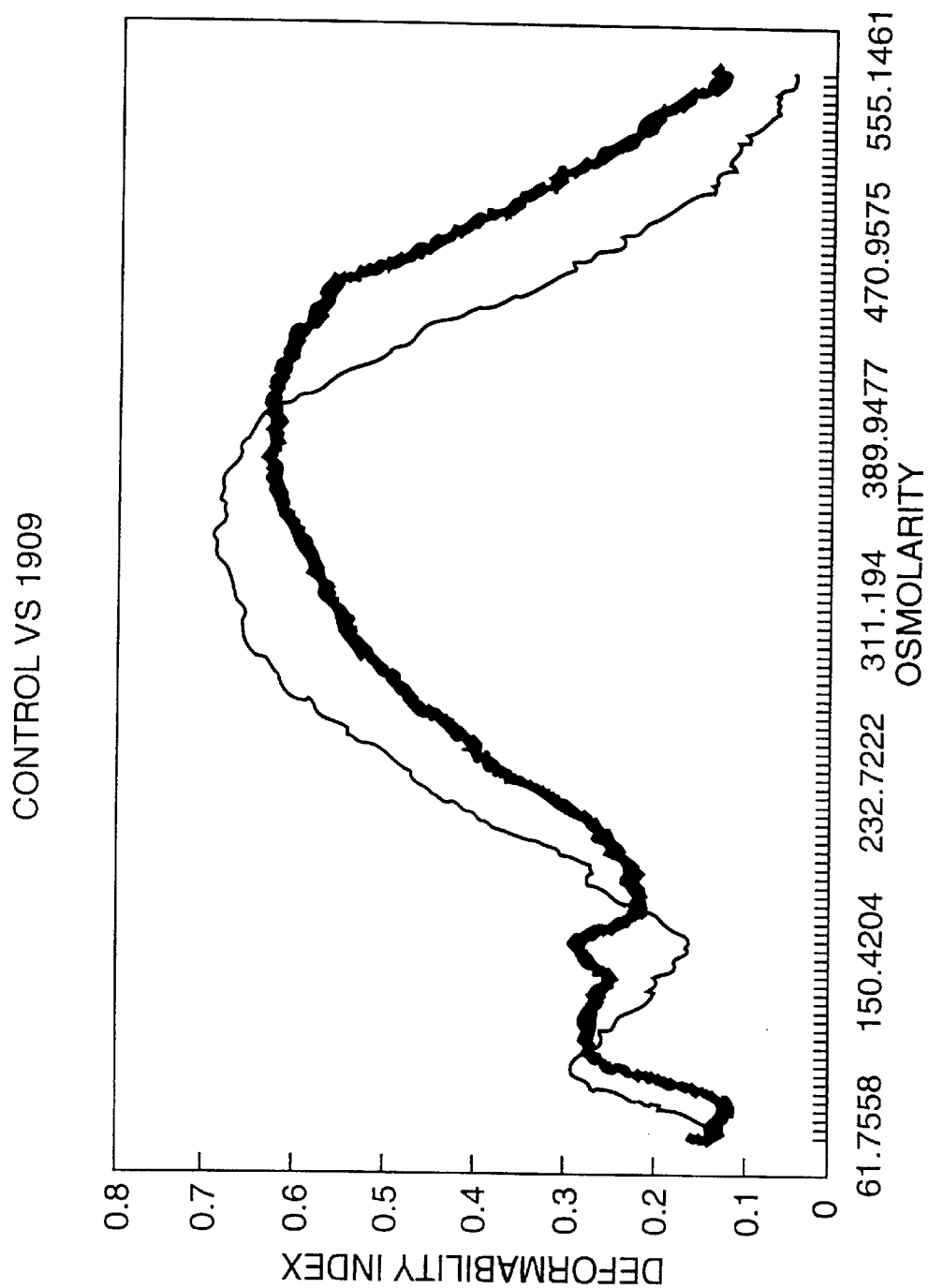
FIG. 3 is an osmoscan profile for rehydrated red cells discribed in Example 6.

In FIG. 3 we show a representative osmoscan profile for the rehydrated red cells in sample SB 1909. The thin-line trace is the response observed with fresh control human red blood cells. The bold-type trace is the response of human red cells dried to at least 10% residual moisture at shelf temperatures ranging from −25° C. and +4° C., and then rehydrated to yield intact and viable red blood cells. From this osmoscan profile it can be seen that the maximum average cell deformability (DImax), corresponding to the peak curve height, is very close (92.6% in Table 10) to that of fresh red cells. In addition, the overall curve profile is very near to that of fresh red cells. From our past experience with this method, we know that grossly rigid, damaged cells or cell debris yield a flat osmoscan profile, with a DImax of 0.3 or less (data not shown). FIG. 3 shows that the recovered rehydrated cells exhibit cellular rheology properties very similar to those of normal, untreated red cells, and this suggests that these cells retain the flexibility needed to survive circulation in the microvasculature following transfusion.

Example 7

In Table 11 we used fresh or one day-old human platelet concentrates to evaluate several polyvinylpyrrolidone (PVP) based cryostabilizing formulations. We combined different carbohydrates with the polymer, including monosaccharides and disaccharides. Hence the monosaccharide provides a membrane permeant cryoprotectant while the polymer and disaccharide are extracellular protectants. All of the PVP-based formulations used with human platelet concentrates comprised a 10,000 average molecular weight PVP (PVP-10). We add these cryoprotectants directly to platelet concentrates in autologous plasma, which contains a buffering system, hence the formulations tested in Table 11 are prepared in 10 mM phosphate buffers, pH 7.2.

In Table 11 we show different cryoprotectant formulations comprising trehalose (tre), glucose (gluc), mannose (man), and/or lactose (lac), expressed in w/v percentages. We mix each buffer in a 1:1 proportion by volume with human platelet concentrate, and all w/v percents given in Table 11 refer to the final component concentration in the mixture of cryoprotectant solution and platelet concentrate. We examined cryoprotectant formulations containing one, two, or three primary cryoprotective components (i.e., carbohydrate or polymer alone, carbohydrate plus polymer, and carbohydrate mixtures plus polymer).

Samples of each mixture of cells and cryoprotectants were frozen at 10° C./minute in a controlled rate freezer to −60° C., and then transferred for storage to either a −80° C. or a −40° C. freezer. Samples were stored for 4–6 days. Each sample was then thawed in a 37° C. water bath, diluted in phosphate buffered saline (PBS) to enable aggregometry analysis (the PVP must be diluted for proper assay conditions), and the cells recovered by centrifugation.

In this example and in the following examples herein, a standard set of cell quality assays are performed on the recovered cells. In Table 11 and our other platelet data herein, we show comparable values obtained from control, untreated fresh platelet concentrates ("FRESH"). Our reported values are the mean±the standard error of the mean (SEM). These assays include:

1) Cell number recovery based on light microscopic examination and counting of the cells.
2) Cell morphology based on light microscopic examination and using the scoring method of Kunicki et al. (1975) Transfusion vol. 15, 414–421.
3) Aggregometry analysis using a Chronolog Lumi-Aggregometer to measure the normal platelet aggregation response to exogenous agonists. We measure the cell response to three treatments: adenosine diphosphate (ADP)+calcium, ristocetin (an antibiotic that causes platelet aggregation), and collagen (the natural substrate that activates platelet aggregation).
4) Hypotonic shock response (HSR), stresses the platelets under hypotonic conditions to measure the degree of cell flexibility. Healthy cells are able to withstand the shock and shrink to their normal cell volume upon return to isotonic conditions.

The data in Table 11 show that the formulations tested were comparable in preserving the measured in vitro properties following frozen storage at −80° C. for 4–6 days. In all cases the post-thaw assay values were about 50% of the control values observed in fresh, untreated platelet concentrates. Reduction in the hypotonic shock response is noted.

Example 8

In Table 12 we compared the properties of human platelets frozen and stored at −80° C., and then thawed and assayed as described in Example 1. We compared the trehalose/mannose/PVP-10 (TMP) formulation and the lactose/mannose/PVP-10 (LMP) formulation from Example 1 to dimethylsulfoxide (DMSO) or glycerol formulations reported in the blood banking literature. Due to the low glass transition temperature of 5% DMSO, cells stored in this medium are normally maintained at −80° C. We observed that the glycerol/glucose formulation resulted in the lowest cell recovery (this highlights the cell-type specificity of cryoprotectant formulation, as our red cell examples herein show the efficacy of low concentrations of glycerol (18–25% v/v) in red cell preservation). The mono- and disaccharide PVP buffers appear comparable in cell recovery to 5% DMSO at the selected storage temperature.

Example 9

In Table 13 we repeated the experiment shown in Table 12, but stored the platelet concentrates at −40° C. The TMP and LMP formulations both have Tg'>−40° C., while the standard glycerol or DMSO solutions have Tg'<<−40° C. (for both the TMP and LMP formulations the measured Tg' by differential scanning calorimetry was about −31° C.). The frozen samples were stored for 5–7 days. The resulting data show that the high Tg' TMP and LMP formulations yield better cell morphology and superior cell aggregation responses than the DMSO frozen cells. This suggests that frozen cell storage at temperatures much higher than conventional liquid nitrogen storage or −80° C. mechanical freezer storage can be achieved by careful use of glass transition theory in cryoprotectant medium formulation.

Example 10

To extend the study in Example 9, we again prepared fresh, one day-old human platelet concentrates mixed 1:1 by volume with the lactose/mannose/PVP-10 formulation (LMP) as described in Example 1 (the solution is formulated as 10% w/v lactose, 5% w/v mannose, 10% w/v PVP-10,000 mM in 10 MW phosphate buffer, pH 7.2, and is diluted into an equal volume of platelet concentrate). We then compared the ability of this formulation to preserve human platelets at elevated frozen storage temperatures as high as −25° C., relative to standard 5% DMSO. In this experiment four independent samples were prepared and frozen for each parameter (fresh controls, DMSO, and LMP), and then stored at three different temperatures: −80° C., −38° C., and −25° C. In Table 14 we show the data obtained after the frozen platelets were stored for 7 days at each temperature, and then thawed and prepared for aggregometry analysis by a single centrifugation step to remove most of the cryoprotectants. In Table 4 the aggregation response values are expressed as chart percentages. Morphology score and percent cell recovery are obtained as described in Example 7.

The data in Table 4 show that DMSO alone fails to adequately preserve measurable in vitro platelet responses, as well as cellular integrity, at elevated frozen temperatures. The high Tg' LMP formulation (Tg' approximately −31° C.) yields improved functional responses after storage at −38° C. and −25° C. relative to DMSO.

TABLE 1

DSC Studies
Several buffer preparations were examined to determine their glass transition temperatures. A summary of the observed values is included in the following table

| Buffer | Tg'Observed | Tg 'Predicted |
|---|---|---|
| 5% Glucose, 10% lactose, 20% Dextran40 | −26.5 | −25.5 |
| 5% Glucose, 10% Lactose,15% Dextran40 | −25.5 | −27.2 |
| 5% Glucose,10%FCS,20% Dextran40 | −24.0 | — |
| 5% Glucose,10% Lactose,20 PVP40 | −32.8 | −31.2 |
| 5% Glucose,10% Lactose, 15% PVP40 | −31.0 | −32.2 |
| 5% Glucose,10% Lactose, 20% HES200 | −30.0 | −28.4 |
| 0–5M Glycerol,7.5% BSA,0.3M Glucose | −52.0 | −51.0 |
| 0.5M Glycerol,0.3M Glucose Less than | −60 | −101 |

Legend to Table 1.
The predicted Tg' values were derived using Equation 1 for the individual components listed. Each buffer also contained buffer salts and metabolites as listed below (Basic Buffer Salts) whose contribution to calculated Tg' is ignored for the purpose of estimating Tg'. The measured Tg' values were obtained by DSC analysis of 2.3:1 dilutions of buffer:water to approximate the ratio of buffer:cell suspension used for cryostabilization of human red blood cells.
Basic Buffer Salts 1.5 mM KH2PO4 0.75 mM glutamine 8.1 mM Na2HPO4 0.75 mM nicotinic acid 0.49 mM MgCl2 10 mM glutathione 10 mM inosine pH=7.4

5 mM adenine

Dextran 40=dextran 40,000 MW (av)
PVP 40=polyvinylpyrrolidone 40,000 MW (av)
FCS=fetal calf serum
HES=hydroxyethyl starch 200,000 MW (av)
BSA=bovine serum albumin

TABLE 2

Three Component Buffers for Red Blood Cell Cryopreservation

| Buffer Components@ | Calculated+ Tg' (° C.) | Measured* Tg' (° C.) |
|---|---|---|
| 1) 5% mannose/10% lactose/ 20% PVP-40 | −30.7 | −30.0, −30.25 |
| 2) 5% fructose/10% lactose/ 20% PVP-40 | −30.8 | N.D.(1) |

TABLE 2-continued

Three Component Buffers for Red Blood Cell Cryopreservation

| Buffer Components@ | Calculated+ Tg' (° C.) | Measured* Tg' (° C.) |
|---|---|---|
| 3) 5% glucose/10% lactose/ 20% PVP-40 | −31.2 | −30.5, −31.0 |
| 4) 5% mannose/10% trehalose/ 20% PVP-40 | −31.1 | N.D. |
| 5) 5% fructose/10% trehalose/ 20% PVP-40 | −31.2 | N.D. |
| 6) 5% glucose/10% trehalose/ 20% PVP-40 | −31.4 | −32.1 (n = I) |
| 7) 5% mannose/10% sucrose/ 20% PVP-40 | −31.8 | N.D. |
| 8) 5% glucose/10% sucrose/ 20% PVP-40 | −32.1 | N.D. |
| 9) 5% fructose/10% sucrose/ 20% PVP-40 | −31.9 | N.D. |

@All buffers include the Basic Salts listed in Table 1 herein. All percentages are (w/v) percents; PVP-40 is 40,000 average MW polyvinylpyrrolidone.
+Calculated Tg' values from Equation 1 herein, taking buffer dilution into account.
*Measured Tg' values from DSC analysis on 2.3: 1 mixtures of buffer:water; separate values are shown from two independent measurements.
(1)N.D. = Not determined. From our data in Table 3 and buffers #1,3,6 above we find good correlation between calculated and DSC measured Tg' values.

TABLE 3

Buffer Tg' Adjustment by Selection of Solute Components

| Buffer Components | Calculated Tg' (° C.) | Measured Tg' (° C.) |
|---|---|---|
| 10% glucose/10% lactose/ 20% PVP-40 | −33.6 | −33.0, −33.5 |
| 10% glucose/10% lactose/ 20% HES-500 | −31.2 | −31.5, −31.75 |
| 5% glucose/10% lactose/ 20% PVP-40 | −31.2 | −30.5, −31.0 |
| 5% glucose/10% lactose/ 10% dextran-40 | −29.6 | −30.25, −30.25 |
| 5% glucose/10% sucrose/ 20% dextran-40 | −26.1 | −26.0, −26.5 |
| 5% mannose/10% sucrose/ 20% dextran-40 | −25.8 | −24.0, −23.75 |
| 5% mannose/10% trehalose/ 20% dextran-40 | −25.1 | −23.75, −24.0 |
| 5% glucose/20% dextran-40 | −22.4 | −21.25, −21.25 |

All buffer components are expressed as (w/v) percentages, and are made in the Basic Salts formulation as outlined in Table 1. Calculated and measured buffer Tg' values are derived as outlined in Table 1.

TABLE 4

PROPERTIES OF RED CELLS STORED AT −80° C. OR −38° C.: BUFFERS 1–3

|  | Expected Values | Buffer #1 @ −80° C. n = 2 | Buffer #1 @ −38° C. n = 2 | Buffer #2 @ −80° C. n = 2 | Buffer #2 @ −38° C. n = 2 | Buffer #3 @ −80° C. n = 2 | Buffer #3 @ −38° C. n = 2 |
|---|---|---|---|---|---|---|---|
| Recov at Recon % | 90% or greater | 94.2 | 87.1 | 95.4 | 83.4 | 96.1 | 84.2 |
| Overall Recov % | 80% or greater | 84.5 | 71.6 | 86.7 | 65.2 | 90.8 | 69.4 |
| Osmotic Stability % | 70% or greater | 65.6 | 34.1 | 49.4 | 36.1 | 61.0 | 43.7 |
| MCV (fl) | 80–100 | 83.0 | 85.0 | 99.1 | 100.1 | 96.4 | 98.8 |
| MCH (pg) | 25–35 | 27.8 | 27.3 | 29.7 | 27.9 | 29.6 | 29.3 |
| MCHC % | 31–37 | 33.4 | 32.3 | 30.0 | 27.9 | 30.7 | 29.6 |
| OXHb % | 100 | 83.2 | 84.0 | 74.4 | 88.5 | 76.3 | 82.8 |
| METHb % | 0 | 0 | 0 |  | 0 | 0 |  |
| HEMICH | 0% | 15.8% | 16.0% | 25.6% | 11.5% | 23.8% | 17.2% |
| DI max | 0.500 or greater | 0.505 | 0.385 | 0.472 | 0.425 | 0.493 | 0.421 |
| % Contr DI | 80% or greater | 82.4 | 62.8 | 72.1 | 64.8 | 75.2 | 64.2 |
| Osmoscan | Normal | Good but no Omin | Good but no Omin | Good but no Omin | Good but no Omin | Good but no Omin | Good but no Omin |
| RFI | 0.650–0.700 | ND | ND | 0.350 | 0.310 | 0.384 | 0.309 |
| % Contr RFI | 80% or greater | ND | ND | 37.2 | 34.3 | 42.6 | 34.2 |
| Density g/ml | 1.095 or greater | 1.103 | 1.105 | 1.101 | 1.098 | 1.101 | 1.099 |

TABLE 5

PROPERTIES OF RED CELLS STORED AT −80° C. OR −38° C.: BUFFERS 4–6

|  | Expected Values | Buffer #4 @ −80° C. n = 2 | Buffer #4 @ −38° C. n = 2 | Buffer #5 @ −80° C. n = 2 | Buffer #5 @ −38° C. n = 2 | Buffer #6 @ −80° C. n = 2 | Buffer #6 @ −38° C. n = 2 |
|---|---|---|---|---|---|---|---|
| Recov at Recon % | 90% or greater | 93.9 | 78.1 | 94.9 | 80.5 | 95.6 | 76.1 |
| Overall Recov % | 80% or greater | 84.4 | 57.6 | 87.2 | 64.0 | 81.0 | 54.4 |
| Osmotic Stability % | 70% or greater | 52.0 | 35.3 | 54.0 | 37.6 | 60.0 | 28.4 |
| MCV (fl) | 80–100 | 97.9 | 101.6 | 97.6 | 99.1 | 96.9 | 102.8 |
| MCH (pg) | 25–35 | 29.5 | 29.5 | 29.6 | 29.5 | 29.3 | 29.1 |
| MCHC % | 31–37 | 30.1 | 29.1 | 30.3 | 29.8 | 30.4 | 28.3 |
| OXYHb | 100% | 76.3 | 82.3 | 75.8 | 78.8 | 80.4 | 76.9 |
| METHb | 0% | 0 | 0 | 0 | 12.9 | 0 | 0 |
| HEMICH | 0% | 23.7% | 17.7% | 24.2 | 8.3% | 19.6% | 23.1% |
| DI max | 0.500 or greater | 0.509 | 0.432 | 0.467 | 0.419 | 0.512 | 0.422 |
| % contr DI | 80% or greater | 77.8 | 65.9 | 71.2 | 64.0 | 78.2 | 64.5 |
| Osmoscan | Normal | Good but no Omin | Good but no Omin | Abnormal | Abnormal | Good but no Omin | Abnormal |
| RFI | 0.650–0.700 | 0.314 | 0.268 | 0.364 | 0.319 | 0.442 | 0.317 |
| % contr RFI | 80% or greater | 38.7 | 29.7 | 40.3 | 35.3 | 49.0 | 35.1 |
| Density g/ml | 1.095 or greater | 1.098 | 1.097 | 1.100 | 1.097 | 1.098 | 1.100 |

TABLE 6

PROPERTIES OF RED CELLS STORED AT −80° C. OR −38° C.: BUFFERS 7–9

|  | Expected Values | Buffer #7 @ −80° C. n = 2 | Buffer #7 @ −38° C. n = 2 | Buffer #8 @ −80° C. n = 2 | Buffer #8 @ −38° C. n = 2 | Buffer #9 @ −80° C. n = 2 | Buffer #9 @ −38° C. n = 2 |
|---|---|---|---|---|---|---|---|
| Recov at Recon % | 90% or greater | 95.7 | 77.2 | 91.1 | 87.1 | 94.3 | 79.4 |
| Overall Recov % | 80% or greater | 85.1 | 55.7 | 78.4 | 71.9 | 81.2 | 57.3 |
| Osmotic Stability % | 70% or greater | 60.3 | 40.5 | 57.6 | 29.7 | 59.8 | 27.2 |
| MCV (fl) | 80–100 | 95.9 | 98.1 | 83.5 | 83.5 | 83.5 | 84.5 |
| MCH (pg) | 25–35 | 30.7 | 29.9 | 27.8 | 27.4 | 27.7 | 27.1 |
| MCHC % | 31–37 | 32.0 | 30.5 | 33.3 | 32.8 | 33.2 | 32.2 |
| OXYHb | 100% | 70.9 | 81.5 | 88.0 | 88.1 | 88.9 | 84.6 |
| METHb | 0% | 0 | 0 | 0 | 0.150 | 0 | 0 |
| HEMICH | 0% | 39.1% | 18.6% | 12.0% | 11.7% | 11.1% | 15.4% |
| DI max | 0.500 or greater | 0.518 | 0.446 | 0.478 | 0.362 | 0.449 | 0.344 |
| % contr DI | 80% or greater | 79.0 | 68.0 | 78.2 | 59.1 | 73.3 | 56.2 |
| Osmoscan | Normal | Good but no Omin | Abnormal | Good but no Omin | Abnormal | Good but no Omin | Abnormal |
| RFI | 0.650–0.700 | 0.479 | 0.334 | ND | ND | ND | ND |
| % contr RFI | 80% or greater | 53.1 | 37.0 | ND | ND | ND | ND |
| Density g/ml | 1.095 or greater | 1.099 | 1.102 | 1.103 | 1.105 | 1.106 | 1.088 |

TABLE 7

Summary of the results obtained with RBC stored at −22° C. in glycerol based cryobuffers. Note that the blood to buffer ratio for all the experiments is 1:3

|  | Expected Values | 25% Gly Stored at −22° C. for 15 hrs | 75% HES 25% Gly 15 hrs at −22° C. | 15% PVP +25% Gly 15 hrs at −22° C. | 7.5% PVP +25% Gly 15 hrs at −22° C. | 7.5% Lac +25% Gly 15 hrs at −22° C. | 7.5% Sucr +25% Gly 15 hrs at −22° C. | 5% Plur + 25% Gly 15 hrs at −22° C. | 75% De +25% Gly 15 hrs at −22° C. |
|---|---|---|---|---|---|---|---|---|---|
| Recovery at Recon | 90% or greater | 98.1 | 95.5 | 94.7 | 89.6 | 97.6 | 95.2 | 97.8 | 93.5 |
| Overall Recovery | 80% or greater | 91.7 | 74.1 | 85.5 | 71.4 | 93.5 | 90.0 | 89.5 | 74.7 |
| Osmotic Stability | 70% or greater | 97.7 | 91.2 | 97.0 | 94.7 | 97.9 | 95.7 | 95.2 | 95.4 |
| E | 56.0 or greater | 89.6 | 67.8 | 82.9 | 67.6 | 91.5 | 86.1 | 85.2 | 71.3 |
| MCV (fl) | 80–100 | 91.4 | 93.1 | 93.0 | 92.1 | 91.8 | 92.9 | 92.1 | 92.5 |
| MCH (pg) | 25–35 | 30.1 | 29.4 | 31.3 | 29.6 | 31.4 | 31.0 | 30.6 | 30.5 |
| MCHC (g/dL) | 31–37 | 33.0 | 31.6 | 33.6 | 32.2 | 34.3 | 33.3 | 33.1 | 33.0 |
| DI max | 0.500 or greater | 0.657 | 0.645 | 0.636 | 0.630 | 0.643 | 0.613 | 0.639 | 0.662 |
| % Control DI max | 80% or greater | 100 | 100 | 99.2 | 98.3 | 100 | 95.6 | 99.7 | 100 |
| Osmscan | Normal | Normal | Normal | Normal | Normal | Normal | Normal | Normal | Normal |
| RFI | 0.700 or greater | 0.940 | 0.860 | 0.840 | 0.800 | 0.900 | 0.880 | 0.840 | 0.860 |
| % Control RFI | 100 | 98.2 | 89.9 | 87.8 | 83.6 | 94.0 | 92.0 | 87.8 | 89.9 |
| # of Samples | n = 6 | n = 1 | n = 1 | n = 1 | n = 1 | n = 1 | n = 1 | n = 1 |

Abbreviations: Gly, Glycerol; Plur, Pluronic acid; Dext, Dextran 40; HBS, Hydroxylethylstarch 250,000; Lac, Lactose; Sucr, Sucrose.

TABLE 8

Summary of the results obtained with RBC stored at −22° C. for 4 days. Note that the blood to buffer ratio for all the experiments is 1:3

|  | Expected Values | 25% Gly Stored at −22° C. for 4 days | 75% HES 25% Gly at −22° C. for 4 days | 15% PVP +25% Gly at −22° C. for 4 days | 7.5% PVP +25% Gly at −22° C. for 4 days | 7.5% Lac +25% Gly at −22° C. for 4 days | 7.5% Sucr +25% Gly at −22° C. for 4 days | 5% Plur + 25% Gly at −22° C. for 4 days | 75% D +25% Gly at −22° C. for 4 days |
|---|---|---|---|---|---|---|---|---|---|
| Recovery at Recon | 90% or greater | 92.9 | 94.9 | 95.3 | 92.4 | 92.7 | 92.3 | 93.7 | 90.6 |
| Overall Recovery | 80% or greater | 87.4 | 82.3 | 87.4 | 78.8 | 88.8 | 86.3 | 84.5 | 65.5 |
| Osmotic Stability | 70% or greater | 97.4 | 97.6 | 95.2 | 96.5 | 96.6 | 95.4 | 95.4 | 94.5 |
| E | 56.0 or greater | 85.1 | 80.3 | 83.2 | 76.0 | 85.8 | 82.3 | 80.6 | 61.9 |
| MCV (fl) | 80–100 | 91.9 | 92.5 | 93.6 | 93.4 | 92.2 | 92.0 | 91.7 | 92.0 |
| MCH (pg) | 25–35 | 31.0 | 30.4 | 32.1 | 30.2 | 30.9 | 30.6 | 30.3 | 30.0 |
| MCHC (g/dL) | 31–37 | 33.6 | 32.9 | 34.4 | 32.3 | 33.5 | 33.2 | 33.0 | 32.6 |
| DI max | 0.500 or greater | 0.656 | 0.634 | 0.617 | 0.631 | 0.533 | 0.466 | 0.602 | 0.662 |
| % Control DI max | 80% or greater | 100 | 98.9 | 96.3 | 98.4 | 82.8 | 72.7 | 93.9 | 100 |
| Osmscan | Normal | Normal | Normal | Normal | Normal | Normal | Normal | Normal | Normal |
| RFI | 0.700 or greater | 0.907 | 0.840 | 0.800 | 0.860 | 0.740 | 0.760 | 0.860 | 0.840 |
| % Control RFI | 80% or greater | 94.8 | 87.8 | 83.6 | 89.9 | 77.3 | 79.4 | 89.9 | 87.8 |
| # of Samples | n = 6 | n = 1 | n = 1 | n = 1 | n = 1 | n = 1 | n = 1 | n = 1 | n = 1 |

Abbreviations: See Table 7

TABLE 9

Effects of 1,2propanediol on the properties of cells stored at −22° C. Table also shows a summary of the results obtained with 20% glycerol in combination with either lactose or 40K PVP Note that the blood to buffer ratio for all the experiments is 1:3 Note also that some of the RBC were rapidly frozen at −80° C. and then stored at −22° C. for 15 hours

|  | Expected Values | 25% 1,2-propanediol 15 hrs at −22° C. | 15% PVP +25% Prp 15 hrs at −22° C. | 7.5% Lact +25% Prp 15 hrs at −22° C. | 7.5% Lact +20% Gly 15 hrs at −22° C. Slow freeze to −20° C. | 7.5% Lact +20% Gly 15 hrs at −22° C. Fast frozen to −80° C. | 15% PVP +20% Gly 15 hrs at −22° C. Slow freeze to −20° C. | 15% PVP +20% Gly 15 hrs at −22° C. Fast freeze to −80° C. |
|---|---|---|---|---|---|---|---|---|
| Recovery at Recon | 90% or greater | 97.5 | 97.5 | 88.7 | 92.9 | 88.6 | 95.1 | 86.2 |
| Overall Recovery | 80% or greater | 95.2 | 90.5 | 83.7 | 88.3 | 59.5 | 80.4 | 49.7 |
| Osmotic Stability | 70% or greater | 93.8 | 96.7 | 94.8 | 97.4 | 93.4 | 96.9 | 94.3 |
| E | 56.0 or greater | 89.3 | 87.5 | 79.4 | 86.0 | 55.6 | 77.9 | 46.9 |
| MCV (fl) | 80–100 | 94.7 | 94.2 | 90.1 | 84.6 | 91.9 | 86.6 | 90.8 |
| MCH (pg) | 25–35 | 31.0 | 30.1 | 31.4 | 30.3 | 25.8 | 28.3 | 25.0 |
| MCHC (g/dL) | 31–37 | 32.8 | 32.0 | 34.9 | 35.8 | 28.1 | 32.7 | 27.6 |
| DI max | 0.500 or greater | 0.639 | 0.639 | 0.540 | 0.589 | 0.642 | 0.598 | 0.633 |
| % Control DI max | 80% or greater | 99.7 | 99.7 | 84.2 | 92.6 | 100 | 94.0 | 99.5 |
| Osmscan | Normal | Normal | Normal | Normal | Normal | Normal | Normal | Normal |
| RFI | 0.700 or greater | 0.917 | 1.0 | 0.720 | 0.920 | 0.600 | 0.940 | 0.608 |

TABLE 9-continued

Effects of 1,2propanediol on the properties of cells stored at −22° C. Table also shows a summary of the results obtained with 20% glycerol in combination with either lactose or 40K PVP Note that the blood to buffer ratio for all the experiments is 1:3 Note also that some of the RBC were rapidly frozen at −80° C. and then stored at −22° C. for 15 hours

|  | Expected Values | 25% 1,2-propanediol 15 hrs at −22° C. | 15% PVP +25% Prp 15 hrs at −22° C. | 7.5% Lact +25% Prp 15 hrs at −22° C. | 7.5% Lact +20% Gly 15 hrs at −22° C. Slow freeze to −20° C. | 7.5% Lact +20% Gly 15 hrs at −22° C. Fast frozen to −80° C. | 15% PVP +20% Gly 15 hrs at −22° C. Slow freeze to −20° C. | 15% PVP +20% Gly 15 hrs at −22° C. Fast freeze to −80° C. |
|---|---|---|---|---|---|---|---|---|
| % Control RFI | 80% or greater | 93.6 | 100 | 73.5 | 96.0 | 62.8 | 98.3 | 63.6 |
| # of Sample | n = 6 | n = 1 | n = 1 | n = 1 | n = 1 | n = 1 | n = 1 | n = 1 |

Abbreviations: See Table 7

TABLE 10

|  | SB 1965 | SB 1966 | SB 1967 | SB 1909 | SB 1907 | SB 1908 | SB 1909 | SB 1910 | SB 1911 | SB 1912 | SB 1909 | SB 1978–20 | SB 1978–10 |
|---|---|---|---|---|---|---|---|---|---|---|---|---|---|
| Comp (all w/ 25% Gly) | 25% Gly alone | 15% SPG 20 | 7.5% pasel | 0.5 G 2.25L 7.25H 200K | .05G .65L 9.3H 200K | .15G 1.15L 8.2H 200K | 0.5G 2.25L 7.25H 200K | .05G .65L 9.3H 500K | .15G 1.15L 8.2H 500K | 0.5G 2.25L 7.25H 500K | 0.5G 2.25L 7.25H 500K | 2.0G 6.0L 12.0H 200K | 1.0G 3.0L 6.0H 200K |
| % Dry | 90 | 90 | 90 | 90 | 90 | 90 | 90 | 90 | 90 | 90 | 90 | 90 | 90 |
| Rec | 8.4 | 17.5 | 21.1 | 50.6 | 24.2 | 32.7 | 41.1 | 29.8 | 19.5 | 26.9 | 53.5 | 39.0 | 54.1 |
| Osm Stab | 58 | 81 | 77.3 | 85.8 | 64.7 | 70.3 | 81.0 | 68.3 | 66.9 | — | 88.8 | 60.3 | 84.1 |
| MCV | 93.2 | 102.1 | 96.4 | 104.8 | 98.0 | 96.1 | 98.6 | 93.1 | 95.0 | 89.8 | 94.5 | 95.9 | 96.4 |
| MCH | 10.4 | 29.3 | 14.1 | 29.2 | 27.0 | 28.0 | 30.8 | 25.2 | 27.3 | 23.0 | 31.0 | 29.2 | 30.2 |
| MCHC | 11.2 | 28.7 | 14.7 | 27.8 | 27.6 | 29.1 | 31.3 | 27.1 | 28.8 | 25.6 | 32.8 | 30.4 | 31.3 |
| DI Max | — | 80.7 | 60.7 | 85.3 | — | — | — | — | — | — | 92.6 | 81.0 | 88.5 |
| Filter | — | — | — | — | — | — | — | — | — | — | 50.0 | 32.0 | 50.0 |

Legend to Table 10
gly = glycerol
SPG20, Paselli = natural starch hydrolysis products
G = glucose
L = lactose
H 500K = hydroxyethyl starch 500,000 MW
H 200K = hydroxyethyl starch 200,000 MW
% Dry = % dryness by weight.
(all numbers for individual buffer components are % w/v for solids and % v/v for glycerol)

TABLE 11

Comparison of PVP buffers
Storage at −80 C. for 4 to 6 days

| N = 4 | FRESH | Single component | | Two components | Three components | |
|---|---|---|---|---|---|---|
|  |  | Trehalose 10% | PVP 10% | PVP 10% Gluc 0.6M | PVP10% Man.2.5% Tre. 5% | PVP10% Man.2.5% Lac. 5% |
| REcovery | 100.00 | 34.63 | 42.25 | 60.27 | 43.25 | 44.83 |
| SEM | 0.00 | 4.60 | 3.17 | 16.23 | 6.71 | 2.47 |
| Morphology | 189.00 | 92.25 | 113.25 | 68.75 | 104.00 | 99.25 |
| SEM | 29.54 | 12.97 | 8.99 | 17.97 | 7.31 | 7.00 |
| ADP + ca | 70.93 | 31.15 | 32.83 | 5.33 | 23.78 | 27.23 |
| SEM | 6.12 | 2.94 | 4.02 | 2.74 | 3.76 | 3.61 |
| Collagen | 84.05 | 46.78 | 51.83 | 19.40 | 38.75 | 38.48 |
| SEM | 3.00 | 4.12 | 5.68 | 3.96 | 2.53 | 3.78 |
| Ristocetin | 83.10 | 32.00 | 36.23 | 30.53 | 26.38 | 29.18 |
| SEM | 3.91 | 6.39 | 1.60 | 11.23 | 4.72 | 3.30 |

TABLE 11-continued

Comparison of PVP buffers
Storage at −80 C. for 4 to 6 days

|  |  | Single component | | Two components | Three components | |
|---|---|---|---|---|---|---|
|  |  | | | | PVP10% | PVP10% |
| N = 4 | FRESH | Trehalose 10% | PVP 10% | PVP 10% Gluc 0.6M | Man.2.5% Tre. 5% | Man.2.5% Lac. 5% |
| HSR | 41.30 | 4.93 | 7.53 | 5.47 | 2.15 | 1.18 |
| SEM | 11.05 | 3.06 | 3.87 | 2.39 | 1.86 | 1.02 |

Recovery = Numerical recovery
Aggregation induced by ADP + Calcium, Collagen, Ristocetin.
HSR = Hypotonic shock response

TABLE 12

Comparison DMSO or Glycerol buffers with Crypopharm buffers at −80° C.

|  |  |  |  | Cryopharm buffers | |
|---|---|---|---|---|---|
| N = 4 | FRESH | DMSO 5% | Glyc. 5% Gluc.0.6M | TMP 10% | LMP 10% |
| REcovery | 100.00 | 61.63 | 33.80 | 43.25 | 44.83 |
| SEM | 0.00 | 6.53 | 7.92 | 6.71 | 2.47 |
| Morphology | 189.00 | 89.00 | 69.67 | 104.00 | 99.25 |
| SEM | 29.54 | 14.34 | 13.68 | 7.31 | 7.00 |
| ADP + ca | 70.93 | 21.53 | 4.40 | 23.78 | 27.23 |
| SEM | 6.12 | 6.90 | 1.34 | 3.76 | 3.61 |
| Collagen | 84.05 | 36.93 | 10.50 | 38.75 | 38.48 |
| SEM | 3.00 | 5.89 | 4.55 | 2.53 | 3.78 |
| Ristocetin | 83.10 | 35.58 | 46.60 | 26.38 | 29.18 |
| SEM | 3.91 | 6.65 | 6.72 | 4.72 | 3.30 |
| HSR | 41.30 | 2.08 | 10.53 | 2.15 | 1.18 |
| SEM | 11.05 | 1.04 | 6.21 | 1.86 | 1.02 |

TABLE 13

Study of stability at different temperature
Storage at −40 C.

| N = 4 | FRESH | DSMO 5% | TMP 10% | LMP 10% |
|---|---|---|---|---|
| REcovery | 100.00 | 44.23 | 36.48 | 43.00 |
| SEM | 0.00 | 5.39 | 2.88 | 2.38 |
| Morphology | 189.00 | 38.00 | 73.75 | 65.50 |
| SEM | 29.54 | 1.27 | 4.52 | 4.37 |
| ADP + ca | 70.93 | 5.83 | 14.48 | 15.20 |
| SEM | 6.12 | 1.92 | 2.81 | 1.79 |
| Collagen | 84.05 | 14.13 | 33.03 | 33.10 |
| SEM | 3.00 | 3.64 | 3.79 | 3.51 |
| Ristocetin | 83.10 | 6.00 | 14.50 | 13.18 |
| SEM | 3.91 | 2.10 | 2.13 | 1.27 |
| HSR | 41.30 | 0.00 | 0.00 | 0.00 |
| SEM | 11.05 | 0.00 | 0.00 | 0.00 |

TABLE 14

| Cell Property | Fresh Controls | DMSO | LMP |
|---|---|---|---|
| Storage at −80° C. (n = 4) | | | |
| −80° C. | | | |
| Cell Recovery | 100 | 55.6 ± 5.3 | 45.2 ± 3.3 |
| Morphology Score | 184 ± 39 | 88 ± 19 | 91 ± 2 |
| ADP Response | 76.7 ± 4.8 | 27.9 ± 5.6 | 26.2 ± 4.7 |
| Collagen Response | 85 ± 3.8 | 37.2 ± 7.8 | 37.6 ± 4.9 |
| Ristocetin Response | 85.8 ± 4.2 | 33.3 ± 8.5 | 28.2 ± 4.3 |
| HSR | 51.2 ± 9.2 | 1.3 ± 1.1 | 1.6 ± 1.3 |
| Storage at −38° C. (n = 4) | | | |
| −38° C. | | | |
| Cell Recovery | 100 | 43.2 ± 7.1 | 44.4 ± 2.7 |
| Morphology Score | 184 ± 39 | 38 ± 1.7 | 63.3 ± 5.3 |
| ADP Response | 76.7 ± 4.8 | 5.1 ± 2.4 | 13.6 ± 1.5 |
| Collagen Response | 85 ± 3.8 | 11.3 ± 3.6 | 34.1 ± 4.5 |
| Ristocetin Response | 85.8 ± 4.2 | 5.9 ± 2.8 | 12.1 ± 1.2 |
| HSR | 51.2 ± 9.2 | 0 | 0 |
| Storage at −25° C. (n = 4) | | | |
| −25° C. | | | |
| Cell Recovery | 100 | 0 | 36.9 ± 3.3 |
| Morphology Score | 184 ± 39 | 0 | 20 ± 2.1 |
| ADP Response | 76.7 ± 4.8 | 0 | 3.2 ± 0.6 |
| Collagen Response | 85 ± 3.8 | 0 | 13.8 ± 0.9 |
| Ristocetin Response | 85.8 ± 4.2 | 0 | 0 |
| HSR | 51.2 ± 9.2 | 0 | 0 |

What is claimed is:

1. A process for freezing cells, cell membranes or cell-like materials comprising the steps of:

freezing an aqueous mixture comprising a plurality of cells, cell membranes or cell-like materials with a cryoprotective component;

wherein said frozen aqueous mixture is characterized by a glass transition temperature of above about −60° C.;

said cryoprotective component containing a saccharide capable of permeating and stabilizing said cells, membranes or cell-like materials;

and a second water-soluble compound impermeable to said cells, cell membranes or cell-like materials; the amount of said second compound in said mixture being in a weight fraction sufficient to overcome the predicted depression in said glass transition temperature of said mixture due to said first compound; and wherein said freezing is performed by lowering the temperature of said mixture to a temperature at, or below said glass transition temperature of said mixture and above the glass transition temperature of water to form a frozen mixture.

2. A process according to claim 1 further comprising the steps of:

a. maintaining said frozen mixture at frozen storage temperatures at or below said glass transition temperature of said mixture; and b. thawing said frozen mixture.

3. A process according to claim 2 further comprising the step of reconstituting and/or washing said cells, cell membranes, or cell-like materials.

4. A process according to claim 1 further comprising the step of drying said frozen mixture by sublimation or evaporation.

5. A process according to claim 1 further comprising the steps of:

a. drying said frozen mixture by either freeze-drying sublimation or evaporation drying to a dried, solid mixture;

b. reconstituting and/or washing said dried solid mixture to recover rehydrated cells, cell membranes, or cell-like materials.

6. A process according to claims 1, 4, 3, or 5 wherein said second compound of said cryoprotective component comprises amorphous or partially crystalline polymers, or mixtures of different polymers.

7. A process according to claim 6 wherein said polymers comprise natural or synthetic polymers.

8. A process according to claim 7 wherein said natural and/or synthetic polymers comprise polymers having average molecular weights greater than 300.

9. A process according to claim 8 wherein said polymer average molecular weights are between 10,000 and 500,000.

10. A process according to claim 7 wherein said natural polymers comprise starch or starch hydrolysis products.

11. A process according to claim 10 wherein said starch comprises hydroxyethyl starch.

12. A process according to claim 7 wherein said natural polymers comprise proteins, gelatin, dextran, or other polymers derived from plant, animal, or microbial sources.

13. A process according to claim 7 wherein said synthetic polymers comprise polyvinylpyrrolidone, polyethylene glycol, or other polymers derived from organic synthesis.

14. A process according to claim 9 wherein said polymers are present in said solution in weight fraction percentages ranging from 1% up to the limit of solubility of said polymer in aqueous solution.

15. A process according to claim 14 wherein said polymer weight fraction percents are in the range of 5%–25%.

16. A process according to claims 1, 4, 2, or 5 wherein said first compound of said cryoprotective component comprises carbohydrates or mixtures of different carbohydrates.

17. A process according to claim 16 wherein said carbohydrates or carbohydrate mixtures comprise monosaccharides and disaccharides.

18. A process according to claim 17 wherein said monosaccharides or disaccharides are each present in a weight fraction percent between 0.01% up to its solubility limit in aqueous solution.

19. A process according to claim 18 wherein said weight fraction percent is between 0.5% and 20%.

20. A process according to claim 17 wherein said monosaccharides are selected from the group comprising 6 carbon hexose sugars.

21. A process according to claim 18 wherein said hexose sugars comprise glucose, fructose, galactose, and mannose.

22. A process according to claim 17 wherein said monosaccharides are selected from the group comprising 5 carbon pentose sugars.

23. A process according to claim 20 wherein said pentose sugars comprise ribose, xylose, arabinose, and ribulose.

24. A process according to claim 17 wherein said disaccharides comprise maltose, lactose, sucrose, and trehalose.

25. A process according to claims 1, 3, 2, or 4 wherein said first compound of said component comprises polyalcohols.

26. A process according to claim 25 wherein said polyalcohols comprise glycerol and 1,3-propanediol.

27. A process according to claim 25 wherein said polyalcohols are present in concentrations between 0.1% and 40% by volume.

28. A process according to claim 27 wherein said polyalcohols are present in the range of 5%–25% by volume.

29. A process according to claims 1, 4, 2, or 5 wherein said component comprises aqueous mixtures of carbohydrates and/or polyalcohols and polymers.

30. A process according to claim 29 wherein said mixture of carbohydrates and/or polyalcohols and polymers comprise membrane permeable and membrane impermeable components.

31. A process according to claim 29 wherein said aqueous mixtures of carbohydrates and/or polyalcohols and polymers further comprise basic salts.

32. A process according to claim 31 wherein said basic salts comprise electrolytes, cofactors, metal cations, metabolites, buffer salts, vitamins, and protein or steroid hormones and growth factors.

33. A process according to claim 31 wherein said aqueous mixtures of carbohydrates and polymers and basic salts are characterized by a glass transition temperature of −60° C. or higher.

34. A process according to claim 33 wherein said glass transition temperature occurs between −45° C. and +45° C.

35. A process according to claim 34 wherein said glass transition temperature is determined by thermal analysis.

36. A process according to claim 35 wherein said thermal analysis measurements comprises differential scanning calorimetry (DSC).

37. A process according to claims 1, 2, 4, or 5 wherein said mixture of cells, cell membranes, or cell-like materials and cryoprotective component is characterized by a glass transition temperature of −60° C. or higher.

38. A process according to claim 37 wherein said mixture has a glass transition temperature between −45° C. and +45° C.

39. A process according to claim 37 wherein said glass transition temperature is measured by differential scanning calorimetry.

40. A process according to claims 1, 4, 3, or 5 wherein said cells comprise mammalian cells.

41. A process according to claim 39 wherein said mammalian cells comprise human cells.

42. A process according to claim 40 wherein said human cells comprise solid tissues.

43. A process according to claim 40 wherein said human cells comprise peripheral blood cells.

44. A process according to claim 42 wherein said peripheral blood cells comprise red blood cells, platelets, stem cells, and leukocytes.

45. A process according to claims 1, 2, 4 or 5 wherein said cell membranes comprise mammalian cell membranes.

46. A process according to claim 45 wherein said mammalian cell membranes comprise human cell membranes.

47. A process according to claim 46 wherein said human cell membranes comprise membranes of peripheral blood cells, including red blood cells, platelets, stem cells, and leukocytes.

48. A process according to claims 1, 4, 2 or 5 wherein said cell-like materials comprise synthetic phospholipid membranes or vesicles.

49. A process according to claim 48 wherein said vesicles comprise liposomes and liposome encapsulated hemoglobin.

* * * * *

UNITED STATES PATENT AND TRADEMARK OFFICE
CERTIFICATE OF CORRECTION

PATENT NO. : 5,958,670
DATED : September 28, 1999
INVENTOR(S) : Raymond P. GOODRICH, et al.

It is certified that error appears in the above-identified patent and that said Letters Patent is hereby corrected as shown below:

Claim 6, col. 31, line 18, "1, 4, 3, or 5" should read --1, 4, 2, or 5--.

Claim 25, col. 31, line 66, "1, 3, 2, or 4" should read --1, 4, 2, or 5--.

Claim 40, col. 32, line 42, "1, 4, 3, or 5" should read --1, 4, 2, or 5--.

Signed and Sealed this

Twenty-fifth Day of April, 2000

Attest:

Q. TODD DICKINSON

*Attesting Officer*　　　　*Director of Patents and Trademarks*